US007338675B2

(12) United States Patent
Lee et al.

(10) Patent No.: US 7,338,675 B2
(45) Date of Patent: Mar. 4, 2008

(54) FENUGREEK SEED BIO-ACTIVE COMPOSITIONS AND METHODS FOR EXTRACTING SAME

(75) Inventors: Steve S. Lee, Sandy, UT (US); Richard B. Hynson, Missoula, MT (US); Ke-Qin Zhang, Fujian (CN); Wu-Zhou Li, Jiangsu (CN); Jing Shi Zhou, Shanghai (CN)

(73) Assignee: TSI Health Sciences, Inc., Missoula, MT (US)

( * ) Notice: Subject to any disclaimer, the term of this patent is extended or adjusted under 35 U.S.C. 154(b) by 0 days.

(21) Appl. No.: 10/434,444

(22) Filed: May 7, 2003

(65) Prior Publication Data

US 2004/0009247 A1    Jan. 15, 2004

Related U.S. Application Data

(60) Provisional application No. 60/379,839, filed on May 10, 2002.

(51) Int. Cl.
    *A01N 65/00* (2006.01)
    *A01N 37/30* (2006.01)
    *A01N 37/12* (2006.01)

(52) U.S. Cl. ............. 424/757; 424/776; 514/556; 514/561

(58) Field of Classification Search ........ 424/757, 424/776, 866; 435/107–110, 113–116; 514/561, 514/909
See application file for complete search history.

(56) References Cited

U.S. PATENT DOCUMENTS

| | | | | |
|---|---|---|---|---|
| 5,449,823 | A | 9/1995 | Lerch | 562/577 |
| 5,470,879 | A | 11/1995 | Sauvaire et al. | 514/561 |
| 5,658,571 | A | 8/1997 | Gopalan et al. | 424/757 |
| 5,997,877 | A | 12/1999 | Chang | 424/757 |
| 6,413,546 | B1 | 7/2002 | He et al. | 424/464 |

FOREIGN PATENT DOCUMENTS

| | | |
|---|---|---|
| EP | 587476 B1 | 3/1998 |
| WO | WO 97/32577 | 9/1997 |
| WO | WO 99/25197 | 5/1999 |
| WO | WO 01/15689 | 3/2001 |

OTHER PUBLICATIONS

Sauvaire et al., Phytochemistry (1984), 23: 479-486. Changes in growth, proteins and free amino acids of developing seeds and pods of fenugreek.*
URL: http://www.tsiinc.com/products/brand/phtml?brand_id =19 (Accessed May 21, 2003) Promilin product information.
URL: http://www.airgreen.co.jp/fenugreek/index_e.html (Accessed Jan. 16, 2003) Fenugreek.
Garti N Et al., "Fenugreek Gum. the magic fiber for an improved glucose response and cholesterol reduction," NutraCos May/Jun. 2002; 1 (3): 5-10.
Belongie L, "Syndrome X Analyzed," HSR Health Supplement Retailer, Apr. 2002.
URL: http://www.sabinsa.com/products/fenusterl.htm (Accessed Apr. 4, 2002).
URL: http://www.kbcincusa.com/BrandNameProducts/Sterofen/STEROFENSpec.htm (Accessed Apr. 2, 2002) Sterofen.
URL: http://www.finsupplements.com/search/Details.asp?RefSite=altdia&ProductID=6 (Accessed Mar. 26, 2002) NatureS Way Blood Sugar with Gymnema.
URL: http://www.chromadex.com/Phytosearch/Fenugreek.htm (Accessed Jan. 17, 2002) Fenugreek.
Billaud et al., "Fenugreek: composition, nutritional value and physiological properties," Sciences des Aliments 2001; 21(1):3-26. [Abstract].
Zupancic et al., "The impact of fertilization on fenugreek yield (Troginella foenum-graecum L.) and diosgenin content in the plant drug," Rostl Vyroba 2001; 47 [Abstract].
Liu F et al., "An extract of *Langerstroemia speciosa* L. has insulin-like glucose uptake-stimulatory and adipocyte differentiation-inhibitory activities in 3T3-L1 cells," Journal of Nutrition 2001; 131(9): 2242-7 [Abstract].
Breil et al., "Effect of 4-hydroxyisoleucine on insulin sensitivity in insulin resistant rats," European Association for the Study of Diabetes, 37th Annual Meeting, Glasgow, United Kingdom, Sep. 9-13, 2001, Abstract: 300.
Andrich VS, "Sports Supplement Review. The Lowdown on Insulin Amplifiers and Glycemic Response Modifiers," Muscle Media Article, Jan.-Feb. 2001.

(Continued)

*Primary Examiner*—Michele Flood
(74) *Attorney, Agent, or Firm*—Pate Pierce & Baird

(57) ABSTRACT

A composition of bio-active compounds and methods for facilitating and supporting the metabolism and transport of glucose and carbohydrates into muscle cells. Preferably, the composition of bio-active compounds include 4-hydroxyisoleucine and one or more amino acids selected from the group consisting of arginine, aspartate, threonine, serine, glutamate, proline, glycine, alanine, cysteine, valine, methionine, isoleucine, leucine, tryptophan, phenylalanine, ornithine, lysine, histidine and gamma-amino butyrate. In one presently preferred embodiment of the present invention, the bio-active compounds are extracted from fenugreek seeds. A method for extracting a composition of bio-active compounds from fenugreek seeds is also disclosed, wherein the method comprises the steps of: (1) providing a plurality of fenugreek seeds; (2) preparing the fenugreek seeds; and (3) extracting a composition of bio-active compounds from the fenugreek seeds, wherein the bio-active compounds comprise 4-hydroxyisoleucine and one or more amino acids selected from the group consisting of arginine, aspartate, threonine, serine, glutamate, proline, glycine, alanine, cysteine, valine, methionine, isoleucine, leucine, tryptophan, phenylalanine, ornithine, lysine, histidine and gamma-amino butyrate. The composition of bio-active compounds and methods for extraction of same preferably include between about 10% and 70% of 4-hydroxyisoleucine and between about 20% and 40% of the amino acids.

57 Claims, 19 Drawing Sheets

OTHER PUBLICATIONS van Loon LJC et al., "Maximizing postexercise muscle glycogen synthesis: carbohydrate supplementation and the application of amino acid or protein hydrolysate mixtures," URL: http://www.acjn.org/cgi/content/abstract/72/1/106 (Accessed Mar. 26, 2002), American Journal of Clinical Nutrition, Jul. 2000; 72(1): 106-11.

van Loon LJC et al., "Plasma insulin reponses after ingestion of different amino acid or protein mixtures with carbohydrate," URL: http://www.acjn.org/cgi/content/abstract/72/1/96 (Accessed Mar. 26, 2002), American Journal of Clinical Nutrition, Jul. 2000; 72(1): 96-105.

Kassem T, et al., "Two key chiral intermediates in a new 4-hydroxyisoleucine synthesis," Acta Crystallographica 2000; C56: 1037-9.

Huang et al., "Determination of two flavone glycosides in the seeds of Trigonella foenum-graecum L. from various production locality," Zhiwu Ziyuan Yu Huanjing Xuebao 2000; 9(4): 53-4. [Abstract].

Broca C, et al., "4-hydroxyisoleucine: Effects of synthetic and natural analogues on insulin secretion," European Journal of Pharmacology 2000; 390: 339-345.

Blumenthal M (ed), "Fenugreek Seed," Herbal Medicine: Expanded Commission E Monographs, American Botanical Council 2000.

Plesman J, "Fenugreek Stabilizes Blood Sugar Levels in Hypoglycemics and Diabetics," Hypoglycemic Health Newsletter. 2000; 16(1): 9-12.

Broca C, et al., "4-hydroxyisoleucine: experimental evidence of its insulinotropic and antidiabetic properties," American Journal of Physiology Oct. 2001; 277(4 Pt 1): E617-23.

Muralidhara et al., "Acute and subchronic toxicity assessment of debitterized fenugreek powder in the mouse and rat," Food and Chemical Toxicology 1999; 37(8): 831-8. [Abstract].

Genet et al., "Effects of vandate, insulin and fenugreek (Trigonella foenum greacum) on creatine kinase levels in tissues of diabetic rat," Indian Journal of Experimental Biology Feb. 1999; 37(2): 200-2. [Abstract].

Raju et al., "Effect of antidiabetic compounds on glyoxalase I activity in experimental diabetic rat liver," Indian Journal of Experimental Biology Feb. 1999; 37(2): 193-5. [Abstract].

Szentmihalyi et al., "Investigation of Troginella foenum-graecum L. Fabacea oil. Comparative evaluation of samples from supercritical and conventional extraction," Olaj, Szappan, Kozmet 1999; 48(5): 204-6. [Abstract].

Panda et al., "Inhibition of triiodothyronine production by fenugreek seed extract in mice and rats," Pharmacological Research Jan. 1999; 40(5): 405-9 [Abstract].

Ravikumar et al., "Effect of fenugreek seeds on blood lipid peroxidation and antioxidants in diabetic rats," Phytotherapy Research May 1999; 13(3): 197-201. [Abstract].

Sowmya et al., "Hypocholesterolemic effect of germinated fenugreek seeds in human subjects," Plant Foods for Human Nutrition 1999; 53(4): 359-65. [Abstract].

Sauvaire Y, et al., "4-hydroxyisoleucine: A novel amino acid potentiator of insulin secretion," Diabetes 1998; 47: 206-10.

Puri D, "Therapeutic potentials of fenugreek," Indian Journal of Physiology and Pharmacology Jul. 1998; 42(3): 423-4. [Abstract].

Taylor et al., "Analysis of steroidal sapogenins from Amber Fenugreek (Trigonella foenum-graecum) by capillary gas chromatography and combined gas chromatography/mass spectrometry," Journal of Agricultural and Food Chemistry 1997; 45(3): 753-9. [Abstract].

Bordia et al., "Effect of ginger (Zingiber officinale Rosc.) And fenugreek (Trigonella foenumgraecum L.) On blood lipids, blood sugar and platelet aggregation in patients with coronary artery disease," Prostaglandins, Leukotrienes, and Essential Fatty Acids May 1997; 56(5): 379-84. [Abstract].

Wang et al., "Studies on chemical constituents of the stems and leaves of Trigonella foenum-graecum L," Zhongguo Zhongyao Zazhi 1997; 22(8): 486-7. [Abstract].

Sauvaire et al., "Steroid saponins from fenugreek and some of their biological properties," Advances in Experimental Medicine and Biology 1996; 405: 37-46. [Abstract].

Rao et al., "Short term nutritional and safety evaluation of fenugreek," Nutrition Research 1996; 16(9): 1495-1505. [Abstract].

Ali Liaquat et al., "Characterization of the Hypoglycemic Effects of Trigonella foenum gracecum Seed," Planta Medica 1995; 61: 358-60.

Khosla et al., "Effect of Trigonella foenum graecum (Fenugreek) on blood glucose in normal and diabetic rats," Indian Journal of Physiology and Pharmacology Apr. 1995; 39(2): 173-4. [Abstract].

Petit et al., "Steroid saponins from fenugreek seeds: extraction, purification, and pharmacological investigation on feeding behavior and plasma cholesterol," Steroids Oct. 1995; 60(10): 674-80. [Abstract].

Pavithran K, "Fenugreek in diabetes mellitus," The Journal of the Association of Physicians of India Jul. 1994; 42(7): 584. [Abstract].

Petit et al., "Effects of a fenugreek seed extract on feeding behavior in the rat: metabolic-endocrine correlates," Pharmacology, Biochemistry, and Behavior Jun. 1993; 45(2): 369-74. [Abstract].

Sauvaire et al., "Implication of steroid saponins and sapogenins in the hypocholesterolemic effect of fenugreek," Lipids Mar. 1991; 26(3): 191-7.

Sharma et al., "Effect of fenugreek seeds on blood glucose and serum lipids in type I diabetes," European Journal of Clinical Nutrition Apr. 1990; 44(4): 301-6. [Abstract].

Swanston-Flatt et al., "Glycaemic effects of traditional European plant treatments for diabetes. Studies in normal and streptozotocin diabetic mice," Diabetes Research Feb. 1989; 10(2): 69-73. [Abstract].

Alcock et al., "Stereochemistry of the 4-hydroxyisoleucine from Trigonella foenum-graecum," Phytochemistry 1989; 28(7): 1835-41.

Riyad et al., "Effect of fenugreek and lupine seeds on the development of experimental diabetes in rats," Planta Medica Aug. 1989: 54(4): 286-90. [Abstract].

Madar et al., "Glucose-lowering effect of fenugreek in non-insulin dependent diabetics," European Journal of Clinical Nutrition Jan. 1988; 42(1): 51-4. [Abstract].

Madar et al., "Dietary fiber," Progress in Food & Nutrition Science 1987; 11(2): 153-74. [Abstract].

Madar Z, "New sources of dietary fibre," International Journal of Obesity 1987; 11 Suppl 1: 57-65. [Abstract].

Ribes et al., "Antidiabetic effects of subfractions from fenugreek seeds in diabetic dogs," Proceedings for the Society for Experimental Biology and Medicine Jun. 1986; 182(2): 159-66.

Ribes et al., "Effects of fenugreek seeds on endocrine pancreatic secretions in dogs," Annals of Nutrition & Metabolism 1984; 28(1): 37-43.

Valette et al., "Hypocholesterolaemic effect of fenugreek seeds in dogs," Atherosclerosis Jan. 1984; 50(1): 105-11.

Hardman et al., "The occurrence of 4-hydroxyisoleucine in steroidal sapogenin-yielding plants," Phytochemistry 1976; 15(2): 325. [Abstract].

Fowden L, et al., "4-hydroxyisoleucine from Seed of Trigonella Foenum-Graecum," Phytochemistry 1973; 12: 1707-11.

Dawidar et al., "Steroid sapogenin constituents of fenugreek seeds," Planta Medica Dec. 1973; 24(4): 367-70. [Abstract].

Sauvaire et al., "Changes in growth, proteins and free amino acids of developing seed and pod of fenugreek," Phytochemistry 1984; 23(3): 479-486.

* cited by examiner

FENUGREEK SEED BIO-ACTIVE COMPOSITIONS AND METHODS FOR EXTRACTING SAME

RELATED APPLICATION

This application claims the benefit of U.S. Provisional Application Ser. No. 60/379,839, filed May 10, 2002, and entitled "BIO-ACTIVE FENUGREEK SEED COMPONENT EXTRACTION METHOD," which is incorporated herein by reference.

BACKGROUND

1. Field of the Invention

This invention relates to methods and compositions affecting metabolism, and more particularly, to novel compositions of bio-active components that support metabolism and the transportation of glucose and carbohydrates in animals and humans which are derived from fenugreek seeds and methods for extracting the same.

2. The Background Art

Fenugreek is one of the oldest medicinal herbs and is native to southeastern Europe, northern Africa, and western Asia, but is widely cultivated in other parts of the world. Fenugreek is known technically as *Trigonella foenum-graecum,* a member of the family Fabaceae, and commonly referred to as Greek hay. As appreciated by those skilled in the art, fenugreek is a legume and typically grows between two to three feet tall with light green leaves and small white flowers. A fenugreek seed pod may contain between ten to twenty small, flat, yellow-brown seeds. Typically, a plant seed is formed having a thick or hard outer coat called a testa and often referred to as a seed coat. The inner portion of the seed coat contains a plant embryo and a nutritive tissue called endosperm, which surrounds the embryo. As the fenugreek seed embryo matures, it consumes endosperm. Fenugreek seeds often have a pungent aroma and may have a bitter taste, which is said to be similar to celery.

Fenugreek has long been used as a medicinal herb and culinary additive in both Asia and the Mediterranean. It is believed that the seed of the fenugreek plant contains many active compounds with pharmaceutical applications such as, for example, iron, vitamin A, vitamin B, vitamin C, phosphates, flavonoids, saponins, trigonelline and other alkaloids. Fenugreek has been taken as a stomach tonic and as a treatment for abdominal ailments. Western scientific research has provided insight into the chemical analysis of fenugreek seeds, together with the extraction of 4-hydroxyisoleucine from Fenugreek seeds, and has suggested some clinical utilities of fenugreek.

Sir L. Fowden conducted research into the analysis of fenugreek. He taught the isolation and purification of 4-hydroxyisoleucine from fenugreek and claimed that it is the principal unbound amino acid contained in the fenugreek seed. (See, Fowden et al, Phytochemistry, 12:1707, (1973).) Further investigation of the prior art suggests that the amino acids of fenugreek seeds may have nutritional value. (See, Sauvaire et al, Nutr Rep Int, 14:527 (1976).) Spectrophotometry methods have also been taught by those skilled in the art in the analysis of steroid sapogenin content of fenugreek seeds and such prior art methods may be generally used in an effort to determine the composition of subfractions of defatted fenugreek. (See, Baccou et al, Analyst, 102:458 (1977); Ribes et al, Proc Soc Exp Biol Med, 182:159 (1986).) In addition, those skilled in the art have used chloroform to extract the amino acid 4-hydroxyisoleucine from fenugreek seeds. (See, Alcock et al, Phytochemistry, 28(7):1835 (1989).) It has been found, however, that chloroform is toxic and generally unacceptable as an extraction method under standards established by the food and drug industry.

Other compounds have also been isolated from fenugreek seeds. In addition to the major isomers (2S, 3R, 4S)-4-hydroxyisoleucine, minor isomers 4-hydroxyisoleucine and amino acids (Lysine, Histidine and Arginine) have been isolated. Later studies have confirmed the presence of 4-hydroxyisoleucine in fenugreek seeds in two diastereoisomers: the major one being the (2S,3R,4S) configuration, representing about 90% of the total content of 4-hydroxyisoleucine, and the minor one being the (2R,3R,4S) configuration. (See, Alcock, Phytochemistry, 28:1835 (1989).)

As appreciated by those skilled in the art, the major isomer (2S, 3R, 4S) is presently interesting with respect to experimental evidence indicating its ability to stimulate glucose-induced insulin secretion in micromolar concentrations through a direct effect on pancreatic beta cell stimulation in a glucose dependent manner. Moreover, 4-hydroxyisoleucine is able to interact and induce additive insulinotropic effects (i.e., stimulating or affecting the production and activity of insulin, only in the presence of supranormal glucose concentrations). (See, Sauvaire et al, Diabetes, 47:206 (1998).) Investigation of the prior art also discloses clinical studies to investigate the use of subfractions of fenugreek in conditions of hyperglycemia, glucosuria and hyperlipidemia which have been performed on rats, dogs and human pancreatic tissue. (See, Shani et al, Arch Intern Pharmacodyn Ther, 210:27 (1974); Ribes et al, Ann Nutr Metab, 28: 37 (1984); Valette et al, Atherosclerosis, 50:105 (1984); Madar, Nutr Rep Int, 29:1267 (1984).) As appreciated by those skilled in the art, clinical studies conducted on fenugreek have focused on investigating a specific subfraction of the fenugreek seed (e.g., testa and endosperm) or, in the alternative, have focused on the specific effect of 4-hydroxyisoleucine in animals and humans with diabetes or a cholesterol disorder.

Studies have also shown that the natural analogue of 4-hydroxyisoleucine is more effective as an antidiabetic agent than a synthetic version. There is, therefore, a suggestion that the therapeutic effects of 4-hydroxyisoleucine are best obtained from extracts of the fenugreek seed. However, using fenugreek seeds as a raw material source for a nutritional supplement presents some difficulties. For example, one such difficulty or disadvantage stems from the fact that a large dose of fenugreek seeds is usually needed in order to obtain therapeutic and other nutritional effects. Patients or consumers are often unwilling to incorporate even de-fatted and de-bitterized seeds into their diet. Mild gastro-intestinal upset may occur at higher doses with non-defatted seeds. Due to the high fiber content of fenugreek seeds, prolonged and high dosage amounts may result in adverse side effects such as flatus or diarrhea.

The binding capabilities of the fiber in fenugreek seeds may also affect nutrient availability, particularly of minerals. As appreciated, external application of fenugreek seed may result in undesirable skin reactions. Thus, it would be an advancement in the art to provide a method for obtaining bio-active and therapeutic compounds from fenugreek seeds, such that undesirable side effects resulting from ingesting the seed or portions thereof can be avoided.

During the aforementioned research investigations, those skilled in the art developed crude methods for extracting 4-hydroxyisoleucine from fenugreek seeds. These prior art methods and extraction techniques have primarily focused on obtaining a "high-purity" extract of 4-hydroxyisoleucine. For example, the extraction of 4-hydroxyisoleucine using adsorption chromatography is known in the art. Such prior art methods, however, tend to yield only small quantities of 4-hydroxyisoleucine and are typically only suitable for small scale laboratory use. As previously described, an alternative extraction method exercised by those skilled in the art uses a toxic organic solvent, such as chloroform, to extract 4-hydroxyisoleucine from fenugreek seeds, whereby contemplating inherent disadvantages to the consumer. Therefore, and as readily appreciated by those skilled in the art, a safer and more commercially practicable method for extraction of 4-hydroxyisoleucine and other bio-active components from fenugreek seeds is therefore needed.

BRIEF SUMMARY AND OBJECTS OF THE INVENTION

A primary object of the present invention is to provide novel compositions and methods for the extraction and separation of bio-active compounds derived from fenugreek seeds which are capable of facilitating increase glucose induced insulin levels.

It is a further object of the present invention to provide novel compositions and methods for the extraction and separation of bio-active compounds from fenugreek seeds which are capable of enhancing insulin sensitivity.

It is a still further object of the present invention to provide novel compositions and methods for the extraction and separation of bio-active compounds from fenugreek seeds which are capable of stimulating the function of glucose transport factor 4.

It is also an object of the present invention to provide novel compositions and methods for the extraction and separation of bio-active compounds from fenugreek seeds that involve an efficient number of steps and which is economical to produce.

In addition, it is an object of the present invention to provide novel compositions and methods for the extraction and separation of bio-active compounds from fenugreek seeds which provides a high potency extract yield.

It is a still further object of the present invention to provide novel compositions and methods for the extraction and separation of bio-active compounds from fenugreek seeds which provides a high quantity extract yield.

It is another object of the present invention to provide novel compositions and methods for the extraction and separation of bio-active compounds from fenugreek seeds which provides an extract purity yield between about ten (10) to seventy (70) percent.

Further, it is an object of the present invention to provide novel compositions and methods for the extraction and separation of bio-active compounds from fenugreek seeds that yields a profile of bio-active compounds including, without limitation, amino acids, proteins and 4-hydroxyisoleucine.

It is a still further object of the present invention to provide novel compositions of bio-active compounds from fenugreek seeds including, without limitation, 4-hydroxyisoleucine, arginine, aspartate, threonine, seine, glutamate, proline, glycine, alanine, cysteine, valine, methionine, isoleucine, leucine, tryptophan, phenylalanine, ornithine, lysine, histidine and gamma-aminobutyrate.

Additionally, it is an object of the present invention to provide novel compositions and methods for the extraction and separation of bio-active compounds from fenugreek seeds which are anti-hyperglycemic.

It is also an object of the present invention to provide novel compositions and methods for the extraction and separation of bio-active compounds from fenugreek seeds which are capable of independently stimulating glucose transport proteins and facilitating the transport of glucose into muscle cells.

It is a further object of the present invention to provide novel compositions and methods for the extraction and separation of bio-active compounds from fenugreek seeds which work synergistically with insulin to stimulate glucose transport proteins and facilitate the transport of glucose into muscles.

It is a still further object of the present invention to provide novel compositions and methods for the extraction and separation of bio-active compounds from fenugreek seeds which assist in the metabolism of glucose and carbohydrates.

Consistent with the foregoing object; and in accordance with the invention as embodied and broadly described herein, one presently preferred embodiment of the present invention comprises novel compositions and methods for extracting bio-active compounds from fenugreek seeks that facilitate and support metabolism and transportation of glucose and carbohydrates. Specifically, one presently preferred embodiment of the composition of bio-active compounds extracted from fenugreek seeds may work either synergistically with insulin, or independent, to stimulate GT-4 receptors located on skeletal muscle cells. The composition, so isolated, is generally comprised of amino acids and proteins. In one presently preferred embodiment of the present invention, particular emphasis is placed on the isolation of a composition of bio-active compounds including, for example, 4-hydroxyisoleucine, arginine, aspartate, threonine, seine, glutamate, proline, glycine, alanine, cysteine, valine, methionine, isoleucine, leucine, tryptophan, phenylalanine, ornithine, lysine, histidine and gamma-aminobutyrate.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DESCRIPTIONS OF THE PREFERRED EMBODIMENTS

Figure 1:
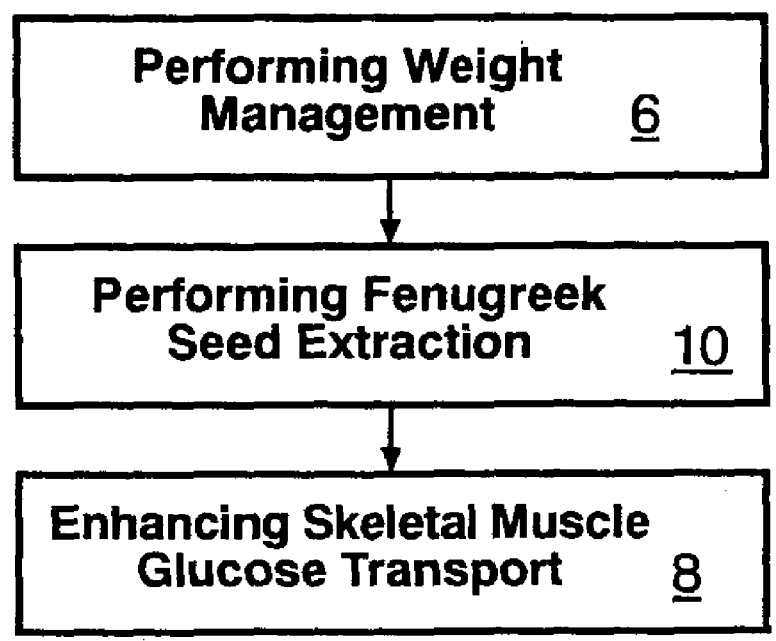
FIG. 1 is a process flow diagram illustrating one presently preferred embodiment of a method of the present invention for weight management by facilitating the transport of glucose into muscle cells and the subsequent metabolism of glucose comprising the steps of providing a composition of bio-active compounds derived from fenugreek seeds, enhancing skeletal muscle glucose transport and performing weight management.

It will be readily understood that the components of the present invention, as generally described and illustrated in the Figures herein, could be arranged and designed in a wide variety of different configurations. Those of ordinary skill in the art will, of course, appreciate that various modifications to the details herein may be made without departing from the essential characteristics of the invention, as described. Thus, the following more detailed description of the embodiments of the compositions and methods of the present invention, as represented in FIGS. 1 through 19, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

The term "diabetes," when used alone, most commonly refers to diabetes mellitus. Diabetes mellitus is commonly referred to as a disorder of carbohydrate metabolism wherein sugars cannot be properly broken down and utilized by the body. The dysfunction in carbohydrate metabolism may generally be associated with a lack of adequate production of insulin. As appreciated by those skilled in the art, insulin is produced by specialized pancreatic cells known as beta cells of islets of Langerhans. Insulin is secreted by the pancreas and moves throughout the body to regulate sugar metabolism and, more particularly, to regulate glucose levels in the bloodstream. Specifically, insulin interacts with several types of cell surface receptors. One such family of receptors is called glucose transport (GT) receptors. At least seven subtypes of the GT receptor family, designated as 1-7 (GT-1-7), have been identified by those skilled in the art.

Many non-diabetic individuals may experience nutritional and metabolic deficiencies during their lifetime which may significantly impact the proper metabolism of glucose and carbohydrates. For example, some individuals may develop a resistance to insulin. These individuals generally have difficulty metabolizing sugars, but not to the level of an individual with diabetes mellitus. One such condition, generally known as "Syndrome X," may be characterized by elevated blood glucose levels and fat deposition, especially in the abdominal area. A condition of elevated blood glucose level is sometimes referred to as hyperglycemic or hyperglycemia. In many non-diabetic individuals experiencing nutritional and metabolic deficiencies, it may be advantageous to facilitate and support the proper metabolism of glucose and other carbohydrates in the body. The facilitation and support of glucose and carbohydrate metabolism may be accomplished with the administration of compositions that work synergistically with existing insulin in the regulation of glucose and other carbohydrate metabolism or, in the alternative, through the administration of compositions that have an effect independent of insulin in the regulation of glucose and other carbohydrate metabolism.

Clinical studies conducted by the inventors of the present invention indicate that novel compositions of bio-active compounds extracted from fenugreek seeds, which contain 4-hydroxyisoleucine and one or more amino acids at certain concentrations, effectively enhance the transport of glucose into skeletal muscle cells in response to the presence of glucose transport factor 4 (GT-4) on skeletal muscle cells. It has been well established that the behavior of cells relative to GT-4 is very strongly correlated to the behavior of a cell relative to insulin. Therefore, a supportable indication that compositions of bio-active compounds extracted from fenugreek seeds may be used to enhance glucose transport into skeletal muscles of humans is a primary focus of the present invention.

In addition, novel compositions of bio-active compounds extracted from fenugreek seeds, which contain 4-hydroxyisoleucine and an array of other amino acids may be combined with glucose or other carbohydrates to alter the physiological responses associated with a bolus administration of glucose or other carbohydrates, or produce unique physiological responses. Physiological responses may include an increase in gut absorption of glucose, stimulation of pancreatic beta cells and enhanced disposal of glucose or other carbohydrates.

Thus, the novel compositions and methods of the present invention support the premise that extracts of bio-active compounds from fenugreek seeds tend to enhance a body's response to insulin and, consequently, that the enhancement of glucose transport to skeletal muscles may be effective in reducing glucose deposited in the liver and adipose tissue, thereby reducing fat deposition.

One presently preferred embodiment of a method for diagnosing and addressing weight management of the present invention, designated generally as 5, is best illustrated in FIG. 1. As shown, a method for weight management contemplating the use of a composition of bio-active compounds derived from fenugreek seeds may comprise the steps of: (1) performing weight management analysis 6 of an individual experiencing nutritional and metabolic deficiencies which impact proper metabolism of glucose and carbohydrates; (2) performing fenugreek seed extraction 10 by means of extracting a composition of bio-active compounds from fenugreek seeds; and (3) enhancing skeletal muscle glucose transportation 8 within the body of the targeted individual by delivery of a composition of fenugreek seed extract.

The step of performing weight management 6 includes diagnosing a condition of ineffective insulin production, insensitivity to insulin or insulin resistance of the targeted individual. Diagnosing may also include recognizing a condition of obesity or the like. In addition, the step of performing weight management 6, as contemplated herein, may further include the periodic administration of one or more compositions of bio-active compounds derived from fenugreek seeds and a suggested modification of the targeted individual's exercise habits and diet.

The step of performing fenugreek seed extraction 10 comprises the step of extracting a composition of bio-active compounds derived from fenugreek seeds, wherein the composition comprises 4-hydroxyisoleucine and an array of other amino acids based on an established ratio. Further, the step of performing fenugreek seed extraction 10 may also include the step of packaging or conditioning of the fenugreek seed extract for consumption by the targeted consumer. For example, the composition extract of bio-active compounds derived from fenugreek seeds may be packaged and presented as a solid (i.e., a pill, powder, tablet or capsule) or dispensed in the form of a liquid, suspension or the like. Providing the novel compositions of fenugreek seed extract may also involve modifying or conditioning the composition extract such that the extract, when introduced into the consumer's body, will reach the targeted tissue in an effective manner. In one presently preferred embodiment of the present invention, a method of fenugreek seed extraction, generally designed as 10, in best illustrated in FIG. 2 and discussed in further detail hereinbelow.

Still referring to FIG. 1, the step of enhancing skeletal muscle glucose transportation 8 within the body of the targeted individual by delivery of one or more novel compositions of fenugreek seed extract contemplates the step of ingesting or otherwise administering (e.g., parenterally) a form of the composition extract and enabling the composition to reach the tissues of the individual such that the fenugreek seed extract facilitates and supports the transport and metabolism of glucose and carbohydrates. As will be discussed hereinbelow, greater concentrations of bio-active compounds in the administered composition yields greater stimulated insulin production, whereby indicating the effectiveness of the novel compositions and methods of producing same in stimulating insulin production in humans.

It will be apparent that a variety of other methods for performing weight management 6, performing fenugreek seed extraction 10 and enhancing skeletal muscle glucose transportation 8 within a targeted individual may be performed in accordance with the inventive principles set forth herein and which are consistent with the spirit and scope of the present invention. It is intended, therefore, that the examples provided herein be viewed as exemplary of the principles of the present invention, and not as restrictive to any particular method, technique, step or ordering of steps for implementing those principles.

Figure 2:
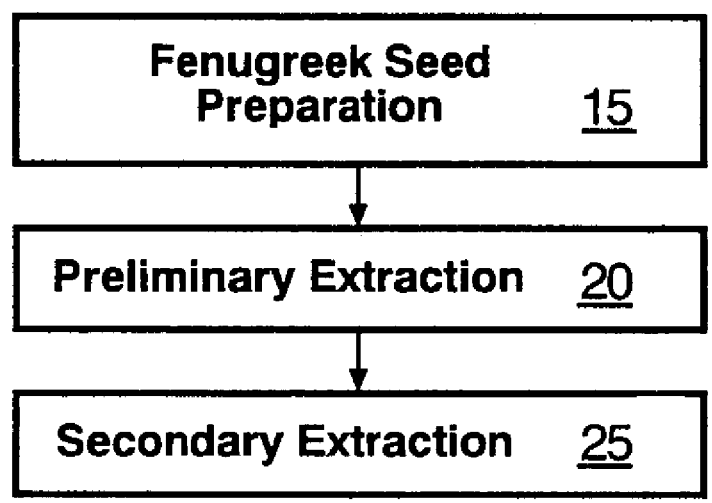
FIG. 2 is a process flow diagram illustrating one presently preferred embodiment of a method of extracting bio-active components from fenugreek seeds of the present invention comprising the steps of fenugreek seed preparation, preliminary extraction and secondary extraction.

One presently preferred embodiment of a method of the present invention for extracting a composition of bio-active compounds, including 4-hydroxyisoleucine and an array of other amino acids, from fenugreek seeds is best illustrated in FIG. 2. Preferably, the method for extracting a composition of bio-active compounds from fenugreek seeds 10 comprises the steps of: (1) preparing the fenugreek seeds 15; (2) performing a preliminary extraction process 20; and (3) performing a secondary extraction process 25. Of course, the extraction method may include other steps, as appreciated by those skilled in the art, in order to more optimally extract those useful bio-active compounds from fenugreek seeds.

Figure 3:
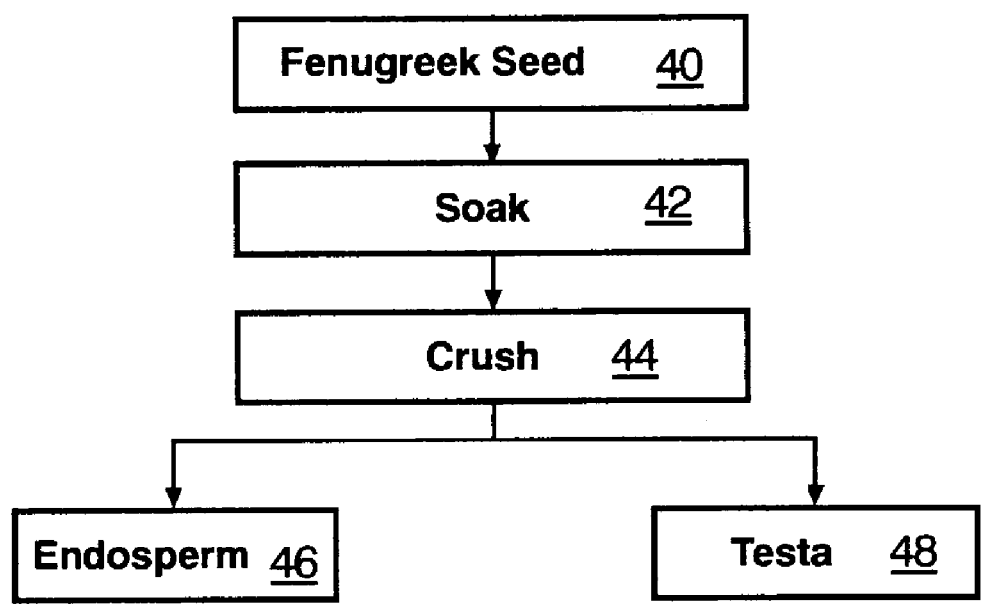
FIG. 3 is a process flow diagram illustrating one presently preferred embodiment of the step for preparing fenugreek seeds of the present invention as referenced in FIG. 2 comprising the steps of soaking the fenugreek seeds in water and then crushing the soaked fenugreek seeds.

Referring now to FIGS. 2 and 3, the step for preparing fenugreek seeds 15 may include the steps of: (1) providing the fenugreek seeds 40; (2) soaking the fenugreek seeds 42; and (3) crushing the fenugreek seeds 44. The soaking step typically involves soaking the seeds in water for a specified amount of time. Other solutions capable of providing the preparative properties of water may also be used. After the seeds have been soaked, the step of crushing the seeds 44 effectively separates various parts of the seed. For example, the crushing step 44 may separate the thick or hard outer coat of the seed, referred to as a testa 48, from the inner portion of the seed, known as the endosperm 46. As appreciated, the endosperm 46 is a nutritive tissue that surrounds the plant embryo.

Figure 4:
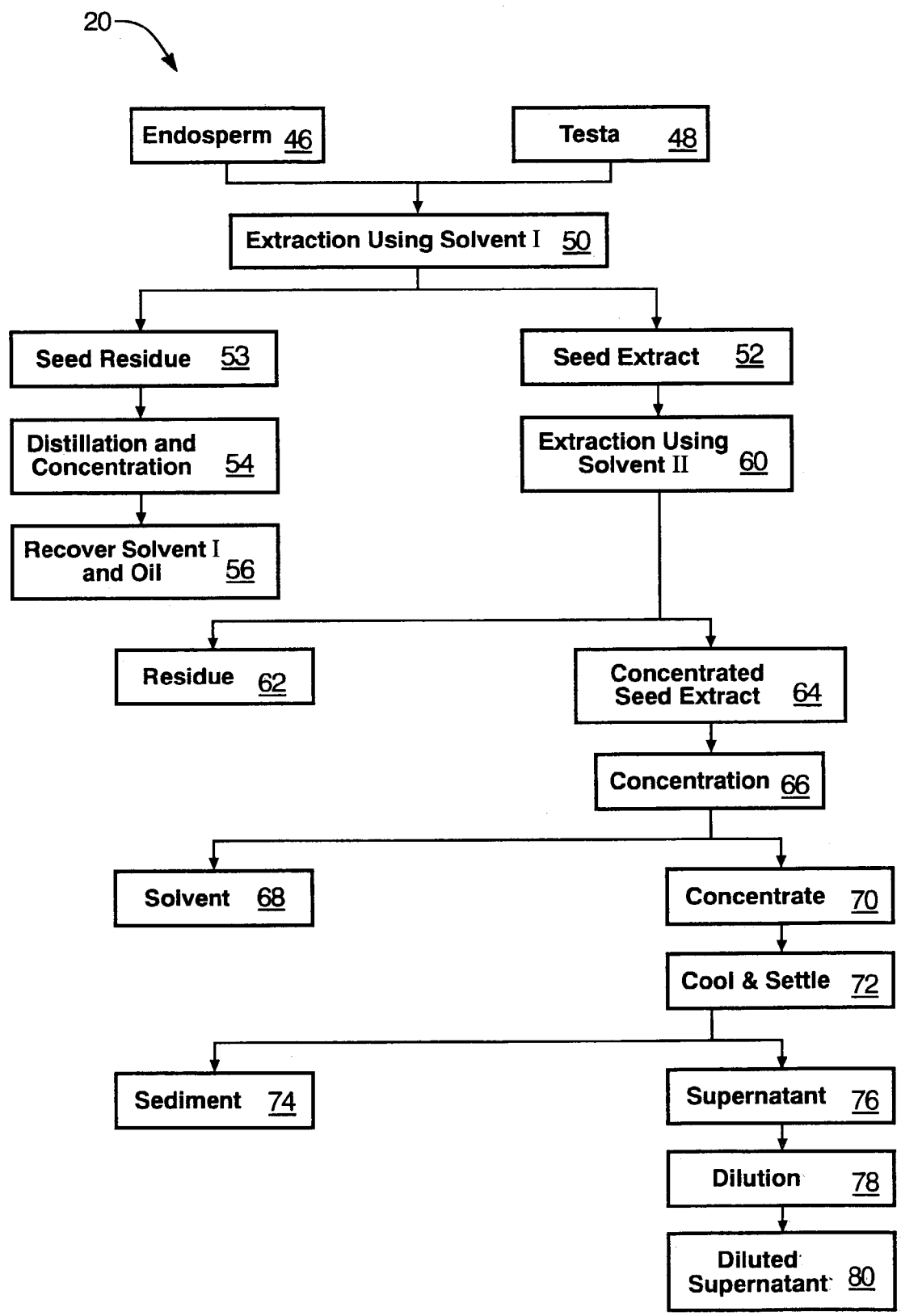
FIG. 4 is a process flow diagram illustrating one presently preferred embodiment of the step of preliminary extraction of the present invention as referenced in FIG. 2 comprising the steps of subjecting the prepared fenugreek seeds to solvent I to obtain a first seed residue and seed extract, subjecting the collected seed residue to solvent II to obtain a second seed residue and a concentrated extract, further concentrating under vacuum, cooling and settling to obtain a sediment of crude proteins and a supernatant and diluting the supernatant with de-ionized water.

Referring now to FIGS. 2 and 4, the step of performing a preliminary extraction process 20 from the endosperm 46 and the testa 48 resulting from the preparation steps 15 may include an extraction step 50 using a solvent (Solvent I). For example, Solvent I may include a compound such as hexane, cyclohexane, ether or any combinations thereof. The extraction step 50, as contemplated herein, effectively de-fats the seeds. Accordingly, after performing the preliminary extraction process 20, the product may be referred to as "de-fatted." The extraction step 50 may also involve repeatedly heating the combination of prepared seeds and Solvent I. In one presently preferred embodiment of the present invention, the combination of seeds and Solvent I may be heated three (3) times to temperatures ranging from between about 20° C. and 90° Celsius (C). More preferably, the combination of seeds and Solvent I may be heated three (3) times to temperatures ranging from between about 65° C. to 70° C. The combination of prepared seeds and Solvent I may be maintained at these elevated temperatures for any of a range of time periods sufficient to achieve the desired results. In one presently preferred embodiment of the present invention, the combination of prepared seeds and Solvent I are maintained at elevated temperatures from about 1 to 3 hours. Consequently, the extraction step 50 typically yields a seed extract 52 and a seed residue 53.

Referring specifically to FIG. 4, a distillation and concentration step 54 may be performed on the fenugreek seed residue 53. As appreciated, the distillation and concentration step 54 may make use of a variety of conventional means to distill and concentrate extracts from the fenugreek seed. For example, distilling a seed residue obtained from successive extractions with a first solvent using a fractionating column may be accomplished by heating the seed residue until boiling, capturing and cooling the heated vapors. The distillation and concentration step 54 may yield quantities 56 of recovered Solvent I, as well as, fenugreek seed oil, diosgenin, fenugreek isoflavone, fenugreek saponin, and a soluble fiber, such as galactomannan or the like.

An extraction step 60 using a solvent (Solvent II) may be performed on the concentrated seed extract 52. Solvent II preferably comprises a solution including ethanol or a solvent having similar chemical properties to ethanol. The concentration of ethanol used in the extraction step 60 may assume a variety of values. For example, the ethanol concentration may vary between the values of about 10% and 95%. In one presently preferred embodiment of the present invention, the extraction step 60 further involves the step of repeatedly heating the combination of seed extract 52 and Solvent II. Preferably, the combination may be heated three (3) times to temperatures ranging from between about 20° C. and 90° C. More preferably, the combination of seed extract 52 and Solvent II may be heated three (3) times to temperatures ranging from between about 65° C. and 70° C. In one presently preferred embodiment of the present invention, the combination of seed extract 52 and Solvent II may be maintained at these elevated temperatures for a broad range of time periods sufficient to achieve the desired results. For example, the combination of seed extract 52 and Solvent II may be maintained at elevated temperatures from about 1 to 3 hours. In this regard, the extraction step 60 typically yields a seed residue 62 and a concentrated seed extract 64.

Additional steps associated with the preliminary extraction process 20 may include a concentration step 66 performed on the concentrated seed extract 64. The concentration step 66 preferably comprises the use of a vacuum to separate quantities of solvent 68 and a concentrate 70. The separated concentrate 70 may then subject to a step of cooling and settling 72 to yield a sediment 74, including crude proteins, and a supernatant 76. A dilution step 78 may then be applied to the supernatant 76 to produce a diluted supernatant 80. As appreciated, the dilution step 78 may involve the addition of de-ionized water. The volume of water added may vary. For example, the amount of water added in one presently preferred embodiment of the dilution step 78 of the present invention may include about 2 to 10 times the volume of the supernatant 76. After dilution, the diluted supernatant 80 may then undergo a secondary extraction process 25, as described in FIGS. 2, 5 and 6.

It will be apparent that a variety of other methods or steps of the preliminary extraction process 20 may be performed in accordance with the inventive principles set forth herein and which are consistent with the spirit and scope of the present invention. It is intended, therefore, that the examples provided herein be viewed as exemplary of the principles of the present invention, and not as restrictive to any particular method, technique, step or ordering of steps for implementing those principles.

Figure 5:
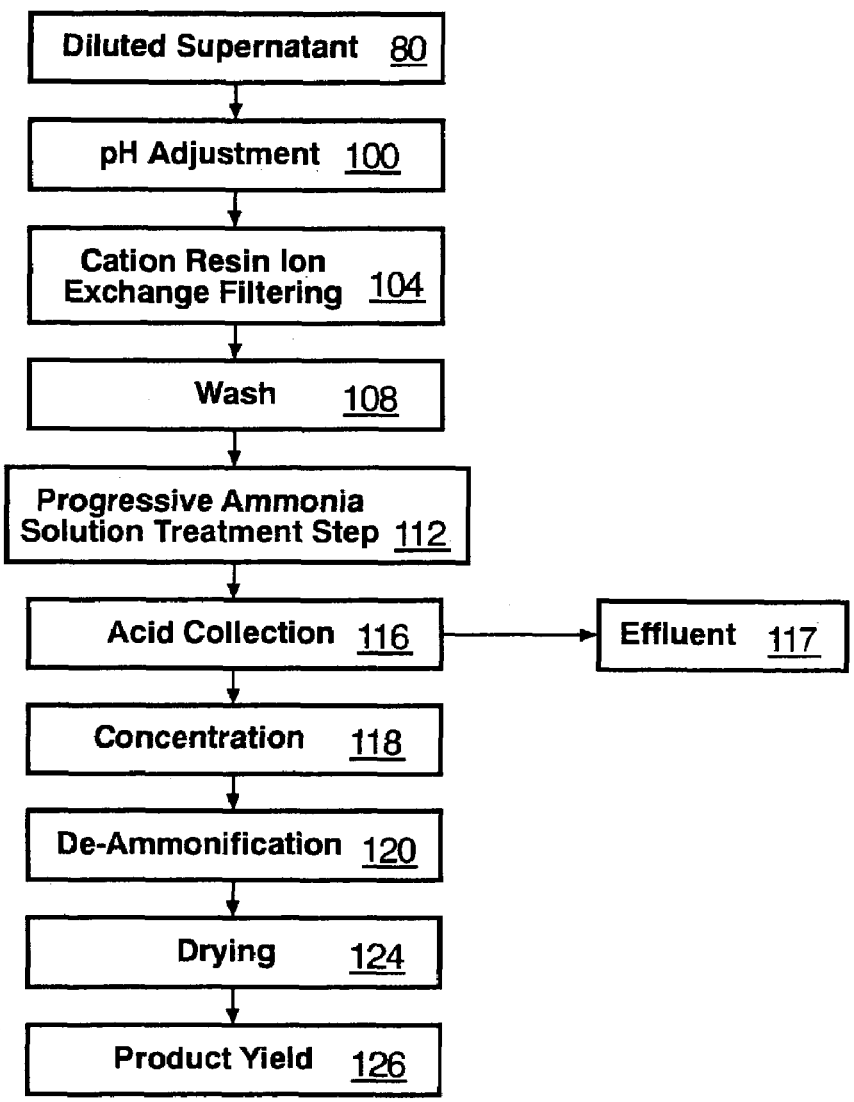
FIG. 5 is a process flow diagram illustrating one presently preferred embodiment of the step of secondary extraction of the present invention as referenced in FIG. 2 comprising the steps of resin filtration with a macropore, non-polar or weakly polar cation ion exchange resin, wash with de-ionized water, progressive ethanol treatment using 10-90% ethanol, effluent collection, pH adjustment to 1-6.5 with 6 Normal (N) hydrochloric acid (HCl), treatment with 0.1-1 N ammonia solution, effluent collection, concentration under vacuum, diluting with de-ionized water, de-ammonification and drying to yield a composition of bio-active compounds containing an array of amino acids including between about 20% and 40% total protein and between about 10% and 70% 4-hydroxyisoleucine.

Referring to FIGS. 2 and 5, the diluted supernatant 80 produced as a result of the preliminary extraction process 20 preferably undergoes a secondary extraction process 25. In one presently preferred embodiment of the present invention, the secondary extraction step 25 may include the step of adjusting the pH 100 of the diluted supernatant 80. The step of adjusting the pH of the diluted supernatant 100 may include the use of a variety of solutions. For purposes of example, and not by way of limitation, hydrochloric acid may be used. The concentration of ingredients of the pH adjusting solution may have a variety of values. As appreciated, the pH of the diluted supernatant 80 may be adjusted to any of a range of values sufficient to accommodate the desired results. Accordingly, the solution of hydrochloric acid may facilitate an adjustment in the pH of the diluted supernatant 80 to a pH in a range of between about 1 and 6.5.

The pH adjusted diluted supernatant 80 may then undergo a cation ion exchange resin filtering step 104. In one presently preferred embodiment, the filtering step 104 involves running the pH adjusted supernatant 80 through a resin. The cation ion exchange resin is typically macroporous and may be weakly polar or non-polar. The treated resin may then undergo a washing step 108 which may include washing the resin with water. The resin may also undergo a progressive ammonia solution treatment step 112, after which an acid collection step 116 may occur. The step of progressive ammonia treatment 112 may contemplate the use of a variety of ammonia solutions. In one presently preferred embodiment, the ammonia solution comprises ammonium water or the like. As appreciated, the concentration of ingredients of the solution may have a variety of values. For example, the concentration of ammonium water may fall within a range of between about 0.1 and 1 N, and preferably about 0.3 N.

The non-acidic effluent 117 of the progressive ammonia solution treatment step 112 may be saved and used for the isolation of nutrients having bio-activity, such as diosgenin, saponins, flavonoids, and soluble fiber, such as galactomannan and the like. Following the acid collection step 116, a concentration step 118 is preferably performed on the acidic portion. As will be appreciated, the concentration step 118 may include using a vacuum.

In one presently preferred embodiment of the secondary extraction process 25 of the present invention, a de-ammonification step 120 may be incorporated to substantially remove ammonia added during previous steps of the fenugreek seed preparation process 10. As appreciated by those skilled in the art, a de-ammonification step 120 may be accomplished by any number of conventional methods. One such method may utilize a macroporous, non-polar column, such as an HDP 100 column. Following the completion of the de-ammonification step 120, a composition of bio-active compounds extracted from the fenugreek seed preparation, which contain 4-hydroxyisoleucine and an array of other amino acids, may be referred to as a debitterized extract.

After de-ammonification, a drying step 124 may be utilized to yield a final product 126 having useful compounds. As appreciated by those skilled in the art, the drying step 124 may utilize any number of methods, for example, spray drying, freeze drying, or drying under vacuum. Typically, the composition of bio-active compounds derived from the prepared fenugreek seeds (e.g., product yield 126) includes both proteins and amino acids. 4-Hydroxyisoleucine is one of such amino acids. More particularly, the product yield 126 preferably includes a composition of bio-active compounds derived from fenugreek seeds, which contains 4-hydroxyisoleucine in proportions of between about 10% and 70% and between about 20% to 40% other proteins in an array of other amino acids. It is therefore possible that a composition of bio-active compounds derived from fenugreek seeds may contain amino acids in proportions of between about 10% and 90%.

It will be apparent that a variety of other methods or steps of the secondary extraction process 25 may be performed in accordance with the inventive principles set forth herein and which are consistent with the spirit and scope of the present invention. It is intended, therefore, that the examples provided herein be viewed as exemplary of the principles of the present invention, and not as restrictive to any particular method, technique, step or ordering of steps for implementing those principles.

Figure 6:
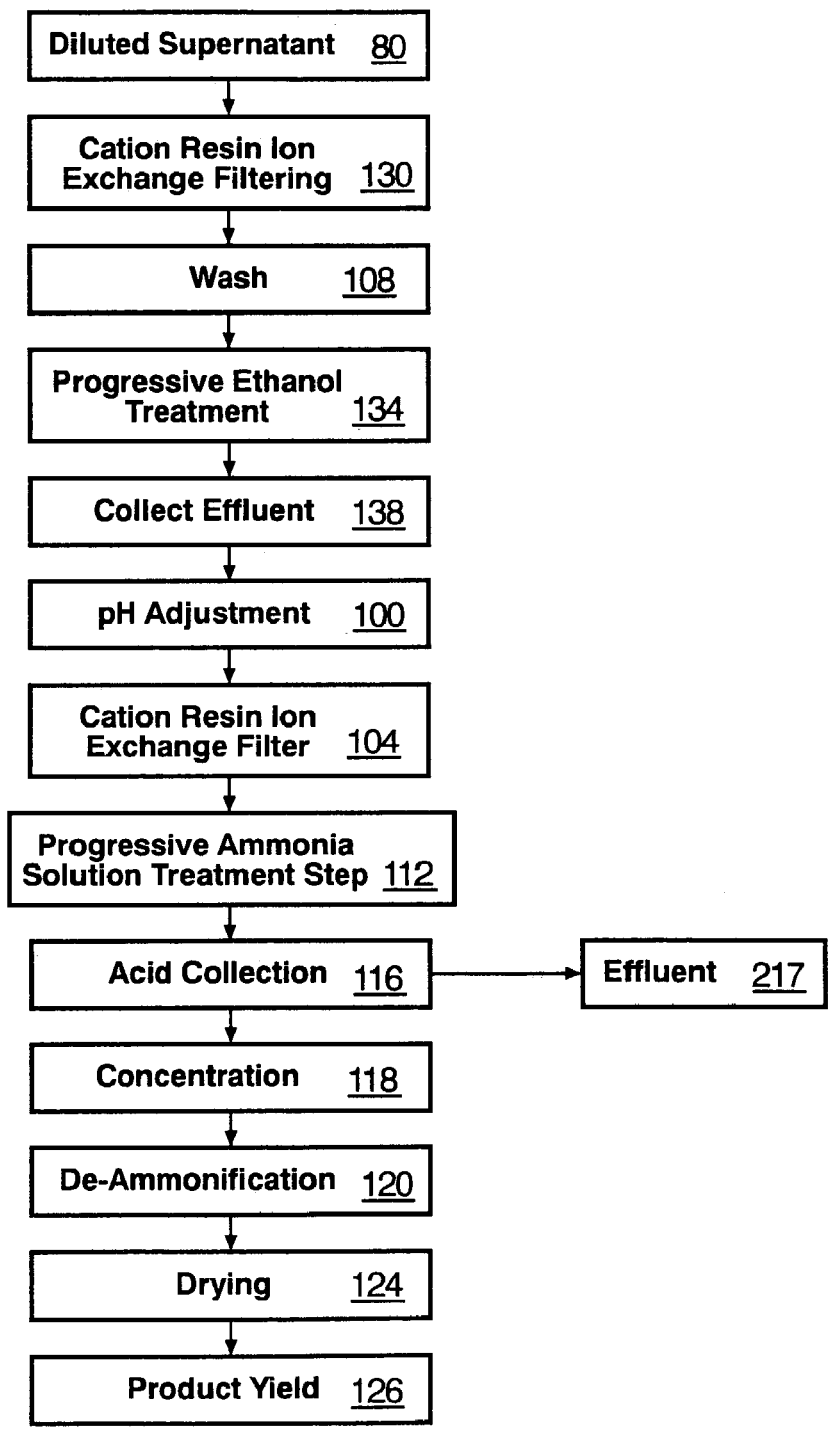
FIG. 6 is a process flow diagram illustrating an alternative presently preferred embodiment of step of secondary extraction as referenced in FIG. 2 comprising the steps of pH adjustment to about 1-6.5 with 6 N HCl, resin filtration with a macropore, non-polar or weakly polar cation ion exchange resin, wash with de-ionized water, treatment with about 0.05 to 2 N ammonia solution, collection of effluent and acidic portion, concentration of the acidic portion under vacuum, de-ammonification and drying to yield a composition of bio-active compounds containing an array of amino acids including between about 20% and 40% total protein and between about 10% and 70% 4-hydroxyisoleucine.

Referring now to FIG. 6, an alternative presently preferred embodiment of a secondary extraction process 125 of the present invention is shown. Specifically, the diluted supernatant 80 produced as a result of the preliminary extraction process 20 preferably undergoes the secondary extraction process 125. In one presently preferred embodiment of the present invention, the secondary extraction step 25 may include a cation ion exchange resin filtering step 130. The filtering step 130 contemplates running the diluted supernatant 80 over or through a resin. The resin is preferably formed having a suitable configuration and is macroporous and either weakly polar or non-polar. The treated resin then undergoes a washing step 108 which may include washing the resin with water.

In one presently preferred embodiment, the resin may also undergo a progressive ethanol treatment step 134. The step of treating the resin with ethanol 134 may involve repeatedly running solvent solutions over the resin. The concentration of ethanol in the solvent is typically increased with each run. As appreciated by those skilled in the art, the step of progressive ethanol treatment 134 may contemplate the use of a variety of suitable substances. For example, ethanol or a solvent having similar applications in bio-active component extraction may be used.

An acid collection step 138 may immediately follow any of the runs of the progressive ethanol treatment step 134 in order to recover nutrients having bio-activity, such as saponins and flavonoids. Typically, the collected effluent 138 of the last run makes use of the highest concentration of solvent and is collected for further processing in accordance with the invention.

The effluent 138 may also undergo the pH adjustment step 100. The step of adjusting the pH 100 of the effluent 138 may include the use of a variety of solutions. For purposes of example, and not by way of limitation, hydrochloric acid may be used. The concentration of ingredients of the pH adjusting solution may have a variety of values. As appreciated, the pH of the collected effluent 138 may be adjusted to any of a range of values sufficient to accomplish the desired results. Accordingly, the solution of hydrochloric acid may facilitate an adjustment in the pH of the effluent 138 to a pH in a range of between about 1 and 6.5.

The pH adjusted solution may then undergo a cation ion exchange resin filtering step 104. In one presently preferred embodiment, the filtering step 104 involves running the pH adjusted solution over or through a cation ion exchange resin having ion exchange properties. The resin is preferably macroporous and may be weakly polar or non-polar. The treated resin may also undergo a progressive ammonia solution treatment step 112, after which an acid collection step 116 may occur. The step of progressive ammonia treatment 112 may contemplate the use of a variety of ammonia solutions. In one presently preferred embodiment, the ammonia solution comprises ammonium water or the like. As appreciated, the concentration of ingredients of the solution may have a variety of values. For example, the concentration of ammonium water may fall within a range of between about 0.1 and 1 N, and preferably about 0.3 N.

The non-acidic effluent 217 of the progressive ammonia solution treatment step 112 may be saved and used for the isolation of nutrients having bio-activity, such as diosgenin, saponins, flavonoids, and soluble fiber, such as galactomannan and the like. Following the acid collection step 116, a concentration step 118 is preferably performed on the acidic portion. As will be appreciated, the concentration step 118 may include using a vacuum.

In one presently preferred embodiment of the secondary extraction process 125 of the present invention, a de-ammonification step 120 may be incorporated to substantially remove ammonia added during previous steps of the fenugreek seed preparation process 10. As appreciated, the de-ammonification step 120 may be accomplished by any number of conventional methods. One such method may utilize a macroporous, non-polar column, such as an HDP 100 column. Following the completion of the de-ammonification step 120, a composition of bio-active compounds extracted from the fenugreek seed preparation, which contain 4-hydroxyisoleucine and an array of other amino acids, may be referred to as a debitterized extract.

After de-ammonification, a drying step 124 may be utilized to yield a final product 126 having useful compounds. As appreciated by those skilled in the art, the drying step 124 may utilize any number of methods, for example, spray drying, freeze drying, or drying under vacuum. Typically, the composition of bio-active compounds derived from the prepared fenugreek seeds (e.g., product yield 126) includes both proteins and amino acids. 4-Hydroxyisoleucine is one of such amino acids. More particularly, the product yield 126 preferably includes a composition of bio-active compounds derived from fenugreek seeds, which contains 4-hydroxyisoleucine in proportions of between about 10% and 70% and between about 20% to 40% other proteins in an array of one or more amino acids.

It will be apparent that a variety of other methods or steps of the secondary extraction process 125 may be performed in accordance with the inventive principles set forth herein and which are consistent with the spirit and scope of the present invention. It is intended, therefore, that the examples provided herein be viewed as exemplary of the principles of the present invention, and not as restrictive to any particular method, technique, step or ordering of steps for implementing those principles.

As appreciated by those skilled in the art, a method validation program may be utilized to quantify the amino acid and protein content of the novel compositions of the present invention. Determination of the ratio of 4-hydroxyisoleucine and other amino acids in fenugreek may be performed using a high performance liquid chromatography (HPLC) apparatus. As contemplated herein, an HPLC apparatus including a fluorescence detector and programmable autosampler may be utilized in a methods validation program. The chromatography column may be a Zorbax stable bond SB-C18 (4.6*150 mm, 5 μm). In addition, an HPLC apparatus may include an analytical balance, accurate to 0.1 mg, an ultrasonic bath, a volumetric flask, a two liter vacuum filtration glassware with 0.2 μm membrane, variable volumetric pipets, and a magnetic stirrer and stir bars.

The reagents of a methods validation program may include, for example: (1) methanol (HPLC grade), (2) acetonitrile (HPLC grade), (3) sodium acetate trihydrate (AR grade), (4) triethylamine (AR grade), (5) glacial acetic acid (AR grade), (6) tetrafuran (AR grade), (7) OPA reagent (Agilent Co. Part No. 5061-3335, containing o-phthaldialdehyde and 3-mercaptopropionic acid in borate buffer), (8) a reference standard of 4-hydroxyisoleucine (obtained from British Agricultural Lab), and (9) de-ionized water.

One presently preferred embodiment of a methods validation program preparation may include a mobile phase step, a standard preparation step, and a sample preparation step. In the mobile phase step, buffer A, buffer B, and a filter/degas step may be utilized. Buffer A may be prepared in a one-litre beaker, wherein 1.36 g of sodium acetate trihydrate may be dissolved in 500 mL water. This combination may be stirred until thoroughly dissolved. 90 μL of triethylamine may be added and mixed. The pH may be adjusted to about 7.2 with 1%-2% of acetic acid solution. 1.5 mL of tetrafuran may then be added and mixed. The final mixture may be labeled—"buffer A."

Buffer B may be formed in accordance with the following procedure. In a beaker, 1.36 g sodium acetate trihydrate may be dissolved in 100 mL of water. This combination may be stirred until thoroughly dissolved. The pH may be adjusted to 7.2 with 1-2% acetic acid solution. 200 mL of methanol and 200 mL of acetonitrile may then be added to the beaker and mixed well. The final mixture may be labeled—"buffer B." Preferably, the buffers may be filtered and degassed using a vacuum and 0.2 μm membrane.

In one presently preferred embodiment of the present invention, a method validation program standard preparation step may include, accurately weighing about 10 mg of a reference compound and placing the compound into a 50 mL volumetric flask. The reference compound may be dissolved using about 30 mL deionized water and undergoing sonicate for approximately 10 minutes. The flask is preferably allowed to cool to room temperature and then the solution may be diluted with water to specific concentration and mixed well. The standard preparation may then be sealed with a parafilm and stored under refrigeration until needed.

A method validation program sample preparation step may include, accurately weighing about 25 mg of a composition of bio-active compounds extracted from fenugreek seed and dissolving with about 30 mL deionized water in a 50 mL volumetric flask and undergoing sonicate for approximately 10 minutes. The flask is preferably allowed to cool to room temperature and then the solution may be diluted with water to specific concentration and mixed well. A sample preparation may be filtered prior to being injected into an HPLC apparatus.

Chromatographic conditions for one presently preferred embodiment of a method validation program may include, for example, a Zorbax stable bond SB-C18 column, a column temperature of 30° C., and an EX 340 nM, EM 450 chromatographic detector. The following gradients and injection program may be utilized:

Gradient:

| Time (min) | % A | % B | F (ml/min) |
|---|---|---|---|
| 0.00 | 100 | 0 | 1.0 |
| 17.0 | 50 | 50 | 1.0 |

-continued

| Time (min) | % A | % B | F (ml/min) |
|---|---|---|---|
| 20.0 | 0 | 100 | 1.0 |
| 20.1 | 0 | 100 | 1.0 |
| 24.0 | 100 | 0 | 1.0 |
| 35.0 | 100 | 0 | 1.0 |

Injection Program:

| Row | Action |
|---|---|
| 1 | Draw 5.0 ul from vial 1 (buffer) |
| 2 | Draw 1.0 ul from vial 2 (sample) |
| 3 | Mix 6.0 ul in air, max. speed, 6 times |
| 4 | Submerge injector tip in vial 11 (wash vial) |
| 5 | Draw 1.0 ul from vial 3 (OPA reagent) |
| 6 | Mix 7.0 ul in air, max. speed, 6 times |
| 7 | Submerge injector tip in vial 11 (wash vial) |
| 8 | Inject |

A method validation program specificity may be performed by examining the spectrum of the identified peak. This peak may show the spectra of the sample and reference standards. A methods validation program linearity may be analyzed preparing standard preparations of 4-hydroxyisoluecine and assayed as directed in the method validation program. One such linearity was undertaken and the following results were observed:

| Concentration (mg/ml) | Peak area | Response (area/conc.) |
|---|---|---|
| 0.09 | 1336.9 | 3.36600e−3 |
| 0.18 | 2654.1 | 3.39098e−3 |
| 0.27 | 4040.7 | 3.34101e−3 |
| y-intercept | −26.56667 | Ave = 3.36600e−3 |
| slope | 300.4222 | SD = 0.024985 |
| correlation | 0.99989 | RSD = 0.74% |

The correlation coefficient is satisfactory (r>0.99950) and these data demonstrate the methods validation program of the present invention has good linearity.

A method validation program precision may be analyzed with six (6) separated tests performed on a test sample, if desired. One such precision analysis was undertaken and the following results were observed:

| 4-OH-Ile precision LOT NO: 2060052 | | |
|---|---|---|
| Number | Peak area | Assay |
| 1 | 2827.8 | 35.4 |
| 2 | 2758.2 | 35.3 |
| 3 | 2997.0 | 34.9 |
| 4 | 2721.5 | 35.1 |
| 5 | 2510.6 | 34.9 |
| 6 | 2562.2 | 35.4 |
| Average | — | 35.2 |
| SD | — | 0.234 |
| RSD | — | 0.66% |

| 4-OH-Ile precision LOT NO: 20020402 | | |
|---|---|---|
| Number | Peak area | Assay |
| 1 | 3369.0 | 43.6 |
| 2 | 3214.2 | 43.9 |
| 3 | 3292.9 | 43.5 |
| 4 | 3112.6 | 43.0 |
| 5 | 3394.8 | 44.1 |
| 6 | 3305.2 | 43.7 |
| average | — | 43.6 |
| SD | — | 0.378 |
| RSD | — | 0.87% |

| 4-OH-Ile precision LOT NO: FSE02G31-32 | | |
|---|---|---|
| Number | Peak area | Assay |
| 1 | 3762.9 | 49.2 |
| 2 | 3574.1 | 48.2 |
| 3 | 3560.3 | 48.2 |
| 4 | 3599.4 | 48.3 |
| 5 | 3629.7 | 49.1 |
| 6 | 3627.1 | 49.1 |
| average | — | 48.7 |
| SD | — | 0.496 |
| RSD | — | 1.00% |

From these results, relative standard deviation (RSD) is <3%. Based on the foregoing, the method validation program delivered good precision for the sample.

A method validation program was conducted and analyzed for reproducibility by testing a same sample with multiple HPLC assays on consecutive days. The following results were observed:

| 4-OH-Ile reproducibility LOT NO: 2060052 | | | |
|---|---|---|---|
| Number | Day 1 | Day 2 | Over 2 days |
| 1 | 35.4 | 34.5 | |
| 2 | 35.3 | 35.7 | |
| 3 | 34.9 | 36.2 | |
| 4 | 35.1 | 34.9 | |
| 5 | 34.9 | 35.6 | |
| 6 | 35.4 | 34.6 | |
| Average | 35.2 | 35.2 | 35.2 |
| SD | 0.234 | 0.683 | 0.489 |
| RSD | 0.66% | 1.94% | 1.39% |

| 4-OH-Ile reproducibility LOT NO: 2002-0402 | | | |
|---|---|---|---|
| Number | Day 1 | Day 2 | Over 2 days |
| 1 | 43.6 | 44.7 | |
| 2 | 43.9 | 43.7 | |
| 3 | 43.5 | 43.9 | |
| 4 | 43.0 | 43.5 | |
| 5 | 44.1 | 43.5 | |
| 6 | 43.7 | 45.0 | |
| Average | 43.6 | 44.0 | 43.8 |
| SD | 0.378 | 0.644 | 0.548 |
| RSD | 0.87% | 1.46% | 1.25% |

The RSD is <3% which shows that the method validation program has good reproducibility.

A method validation program was conducted and analyzed for recovery and accuracy using spiked and recovered sample analyte and spiked and recovered standard analyte. The following results were observed:

| | 4-OH-Ile Recovery | | | | |
|---|---|---|---|---|---|
| | Sample Spiked (mg) | Spiked (4-OH ILE) (mg) | Recovered (4-OH ILE) (mg) | Recovery (4-OH ILE) (%) | Average (%) |
| FSE2060052 + | 10.8 | 5.34 | 5.23 | 98.0 | 97.9 |
| FSE02G31-32 | 22.1 | 10.92 | 10.68 | 97.8 | |
| | 33.9 | 16.75 | 16.41 | 98.0 | |
| FSE20020402 + | 10.2 | 5.04 | 4.98 | 98.7 | |
| FSE02G31-32 | 21.6 | 10.67 | 10.37 | 97.2 | |
| | 30.8 | 15.22 | 14.84 | 97.6 | |

These foregoing data demonstrates that the method validation program of the present invention has good accuracy.

Based on the foregoing results of the method validation program, two lots containing a composition of bio-active compounds derived from fenugreek seed extracted in accordance with the fenugreek seed preparation process 10 of the present invention may be analyzed and the following results may be observed:

| Amino Acid | % | % |
|---|---|---|
| Arginine | 1.09 | 0.90 |
| Aspartate | 1.82 | 1.49 |
| Threonine | 0.41 | 0.35 |
| Serine | 1.71 | 4.44 |
| Glutamate | 3.09 | 2.47 |
| Proline | 0.20 | — |
| Glycine | 0.94 | 0.81 |
| Alanine | 1.48 | 1.22 |
| Cysteine | 0.79 | 0.67 |
| Valine | 0.46 | 0.41 |
| Methionine | 0.15 | 0.20 |
| Isoleucine | 0.21 | 0.20 |
| Leucine | 0.20 | 0.17 |
| Tryptophan | 0.81 | 0.69 |
| Phenylalanine | 0.73 | 0.61 |
| Ornithine | 0.06 | 0.04 |
| Lysine | 0.17 | 0.13 |
| Histidine | 0.16 | 0.14 |
| y-aminobutyrate | 0.34 | 0.29 |
| 4-hydroxyisoleucine | 26 | 23.26 |
| Total % | 40.82 | 36.49 |

Figure 7:
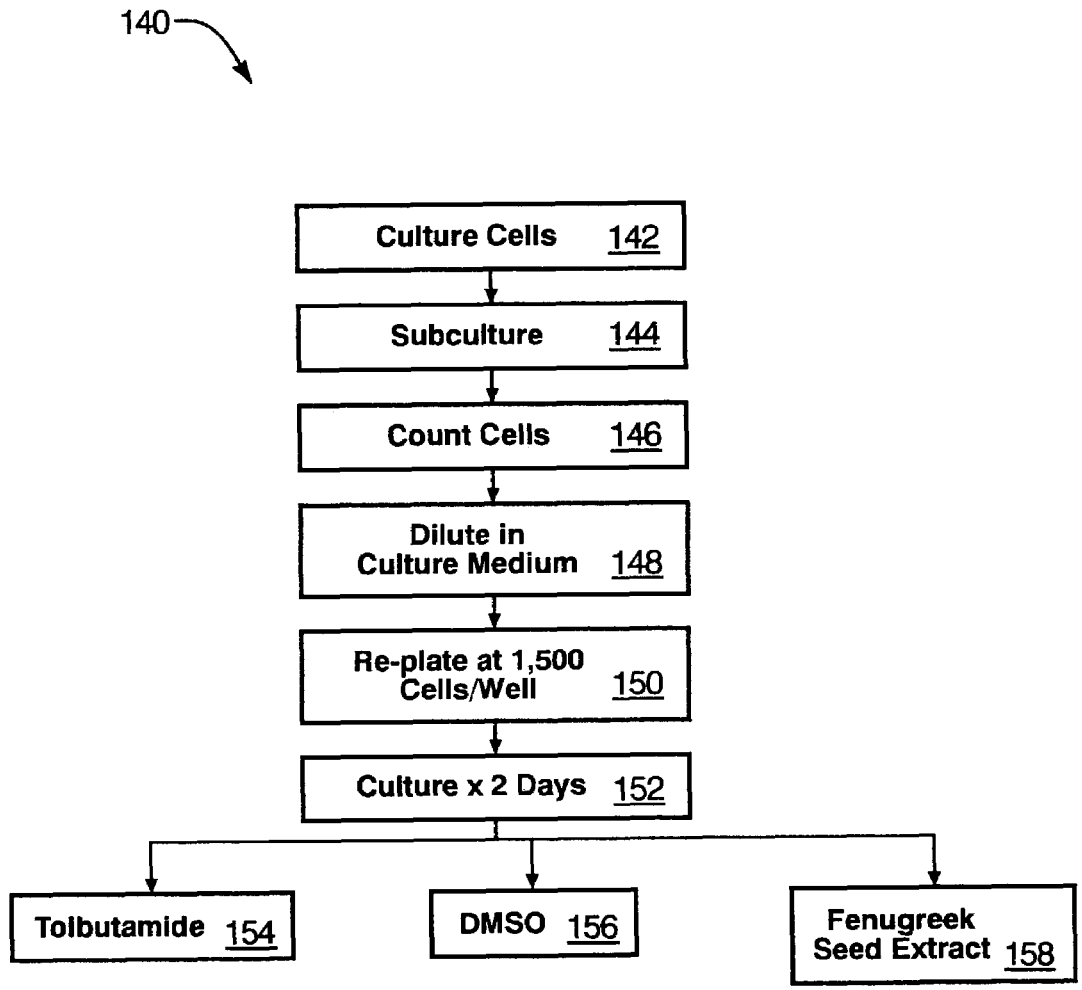
FIG. 7 is a process flow diagram illustrating one presently preferred embodiment of a method of the present invention for culturing pancreatic beta ($\beta$)-cells from a Syrian golden hamster (*Mesocricetus auratus*)
Figure 8:
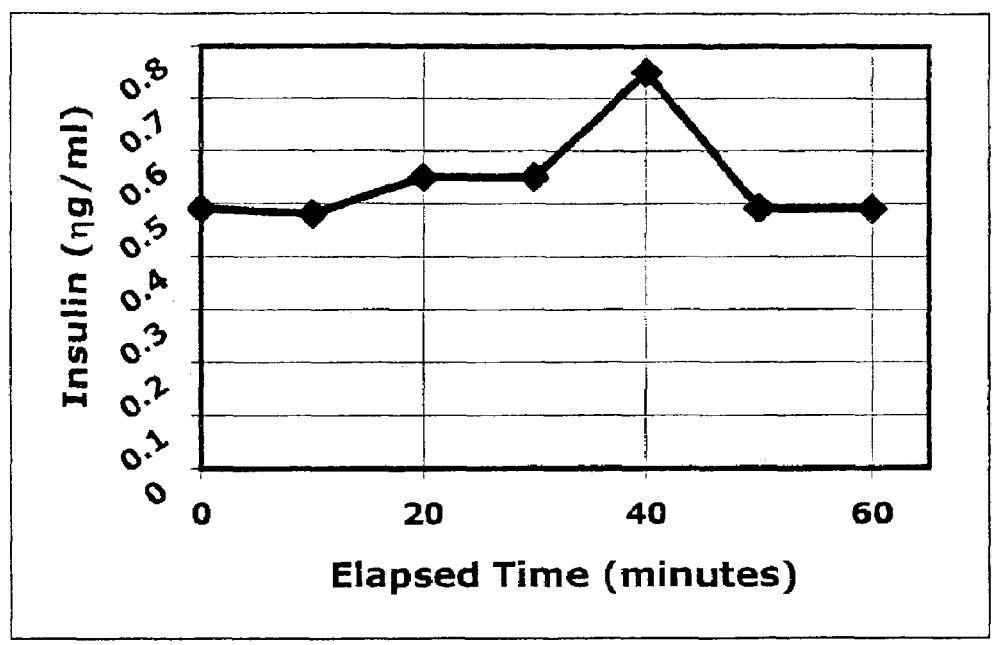
FIG. 8 represents a graph showing the results of tests conducted using cultured pancreatic beta cells from a Syrian golden hamster exposed to a composition of bio-active components derived from fenugreek seeds at a concentration of 15 milligram (mg) per milliliter (mL)
Figure 9:
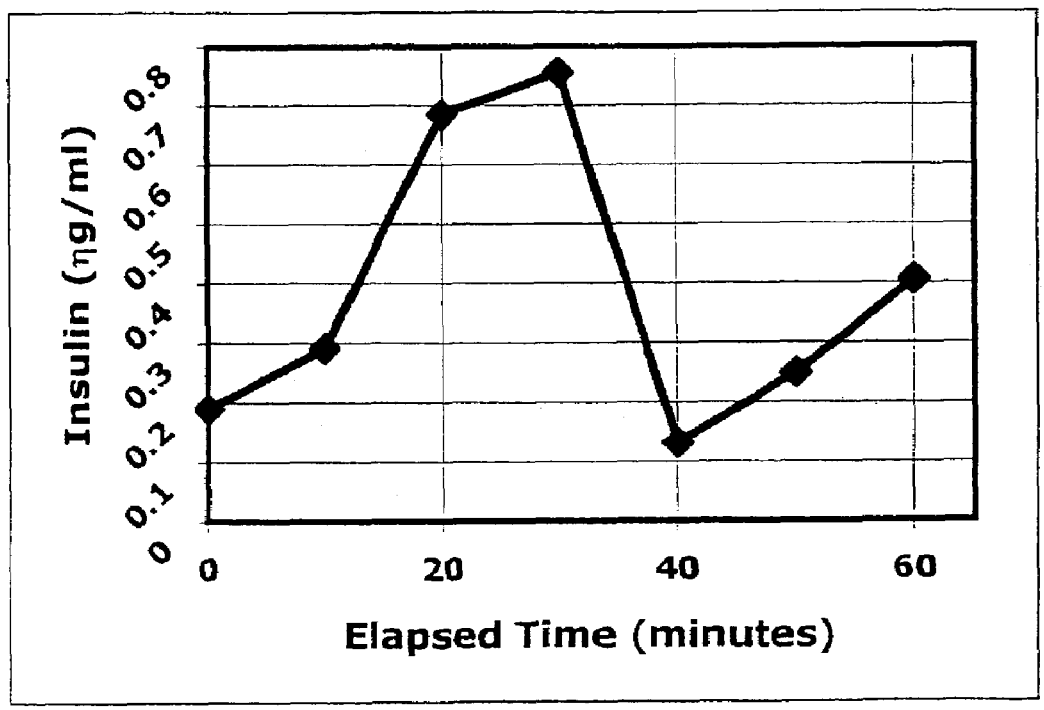
FIG. 9 represents a graph showing the results of a test using a composition of bio-active components derived from fenugreek seeds at a concentration of 60 mg per ml which yielded similar results to the test results shown in the table in FIG. 8.

Referring to FIGS. 7-9 which represent graphical data representing the results of tests conducted on Syrian golden hamster pancreatic tissue, and referring to FIGS. 10-19 which represent graphical data representing the results of clinical tests conducted on human subjects, there is data indicating that the novel compositions of bio-active compounds derived from fenugreek seeds and extracted according to the presently preferred methods disclosed herein effectively facilitate and support glucose and carbohydrate metabolism by independently stimulating GT-4 and also work synergistically with insulin to stimulate GT-4.

The following examples will illustrate the practice of the present invention in further detail. It will be readily understood by those skilled in the art that the following methods, formulations, and compositions of a unique, high-potency, bio-active fenugreek seed extract of the present invention, as generally described and illustrated in the Examples herein, are to be viewed as exemplary of the principles of the present invention, and not as restrictive to a particular structure or process for implementing those principles. Thus, the following more detailed description of the presently preferred embodiments of the methods, formulations, and compositions of the present invention, as represented in Examples I-VI, is not intended to limit the scope of the invention, as claimed, but is merely representative of presently preferred embodiments of the invention.

EXAMPLE I

Syrian Golden Hamster—15 mg/mL

A unique, high-potency bio-active extract is prepared from fenugreek seeds according to a presently preferred embodiment of a fenugreek seed preparation process 10 of the present invention. More particularly, a concentration of 15 mg 4-hydroxyisoleucine per mL is prepared from the yield of process 10. This concentration is administered to an in vitro cell line: HIT-T15, a Syrian golden hamster pancreatic islet of Langerhans beta cell and evaluated for changes in the concentration of insulin activity over time.

Referring now to FIG. 7, a procedure for preparing a cell culture and evaluating the bio-activities of fenugreek extract in cultured pancreatic beta cells from a Syrian golden hamster 140 is illustrated. In one presently preferred embodiment of the present invention, a cell culture 142 from HIT-T15 may be obtained and the cells may be subcultured 144 by removing a growth medium and adding about 4 mL of a solution containing about 0.05% trypsin and 0.53 mM EDTA and gently washing for approximately 5 seconds. The solution may be removed and 4 mL of fresh solution may be added. The cells may be incubated at about 37° C. for approximately 7 minutes. Following detachment, the harvested cells are counted 146 in a manner readily known to those skilled in the art. Once such manner may utilize a Tryptan Blue exclusion method with a hemacytometer. Next the harvested cells are preferably diluted in culture medium 148. A culture medium may comprise Ham's F-12, which is sometimes referred to as Knight's modification or F12K. The cell dilution may be re-plated at 1,500 cells per well 150 in a 24-well plate. Unused cells may then be placed into a 75 cm$^2$ flask. The well plates may continue in culture 152 for about 2 days. Following the completion of the continue in culture 152, the cultured pancreatic beta cells from a Syrian golden hamster may be subjected to tolbutamide 154 and DMSO 156 as positive and negative controls, respectively, and may also be subjected to a concentration of fenugreek seed extract 158.

Referring now to FIG. 8, a graph representing the results of test conducted using pancreatic beta cells from a Syrian golden hamster cultured according to the preparatory procedure 140 and evaluated following exposure to a concentration of a composition of bio-active compounds derived from fenugreek seed extract at 15 mg 4-hydroxyisoleucine per mL is shown. As can be seen from the plot, after addition of the components at time equals zero, insulin levels grew steadily until peaking at time equals 40 minutes and then falling to the insulin level measured before the addition of the components. As appreciated by those skilled in the art, and as depicted in FIG. 8, measurements taken of the insulin activity level in a pancreatic beta cell of a Syrian golden hamster over the course of the experiment indicate that the composition of bio-active compounds derived from fenugreek seed affects the level of insulin in an animal subject.

EXAMPLE II

Fenugreek Seed Extract in Syrian Golden Hamsters—60 mg/mL

As previously described in Example I and as illustrated in FIG. 7, a preparatory procedure 140 was used to culture, harvest, and evaluate pancreatic beta cells from a Syrian golden hamster. Referring now to FIG. 9, a schematic graph illustrates the results from this test. Pancreatic beta cells from a Syrian golden hamster were cultured according to the preparatory procedure 140 and evaluated following exposure to a concentration of the bio-active components of a fenugreek seed extract (e.g., Promilin™) at 60 mg 4-hydroxyisoleucine per mL. As shown, greater concentration of bio-active compounds yielded greater stimulated insulin production. As appreciated by those skilled in the art, and as depicted in the illustration, measurements taken of the insulin activity level in a pancreatic beta cell of a Syrian golden hamster over the course of the experiment indicate that the bio-active components do affect the level of insulin in an animal subject.

It is readily appreciated that tests conducted using pancreatic beta cells from a Syrian golden hamster cultured according to the presently preferred embodiments of the preparatory procedure 140 of the present invention and evaluated following exposure to a concentration of a composition of bio-active compounds derived from fenugreek seed extract (e.g., Promilin™) prepared in accordance with the fenugreek seed preparation process 10 may be configured to apply to any number of embodiments for practicing the present invention which are consistent with the spirit and scope of the present invention. It is intended, therefore, that the examples provided herein be viewed as exemplary of the principles of the present invention, and not as restrictive to a particular structure or method for implementing those principles.

EXAMPLE III

Non-Debitterized Fenugreek Seed Extract in Humans—1 mg 4-hydroxyisoleucine/kg Generally referring now to FIGS. 10-19, tests were conducted with three healthy male human subjects who had no history of diabetes or carbohydrate metabolism dysfunction. The test included two procedures. For the first procedure the subjects fasted overnight. Blood samples were taken from the subjects for glucose and insulin level measurements at time equal to negative 30 minutes, 0 minutes, 15, 30, 60 minutes, 120 minutes, and 180 minutes. At time equal zero, a solution of 75 gram (g) of glucose in 300 mL water was administered to the subjects. The insulin content of each of the blood samples was measured using Radioimmunassay (RIA) at the School of Pharmacy at University of Montana. The results of the blood sample testing is graphically summarized in FIGS. 10-20 as the "placebo portion" data points. As appreciated by those skilled in the art, this type of test is similar to an oral glucose tolerance test (OGTT), which is used in the diagnosis of diabetes and gestational diabetes. In the presently preferred embodiment of the present invention, the first procedure serves as a control mechanism to quantify the baseline level of blood glucose and concentration of insulin activity.

The second procedure was performed under the same conditions as the first procedure. The only difference being that a composition of bio-active compounds derived from fenugreek seed (e.g., Promilin™) were administered to three human subjects. Again, referring generally to FIGS. 10-19, the active solution contained 75 g of glucose in 300 mL of water as well as a dose of fenugreek extract (e.g., Promilin™) between 1-9 mg 4-hydroxyisoleucine per kg of subject body weight. The results of the second procedure are summarized in FIGS. 10-19 as the "active portion" data points.

In one presently preferred embodiment of the present invention, a unique, bio-active non-debitterized fenugreek seed extract composition (e.g., Promilin™) containing an array of twenty amino acids including 1 mg 4-hydroxyisoleucine per kg body weight was administered to human individuals. The resulting composition was administered to a first human subject.

Figure 10:
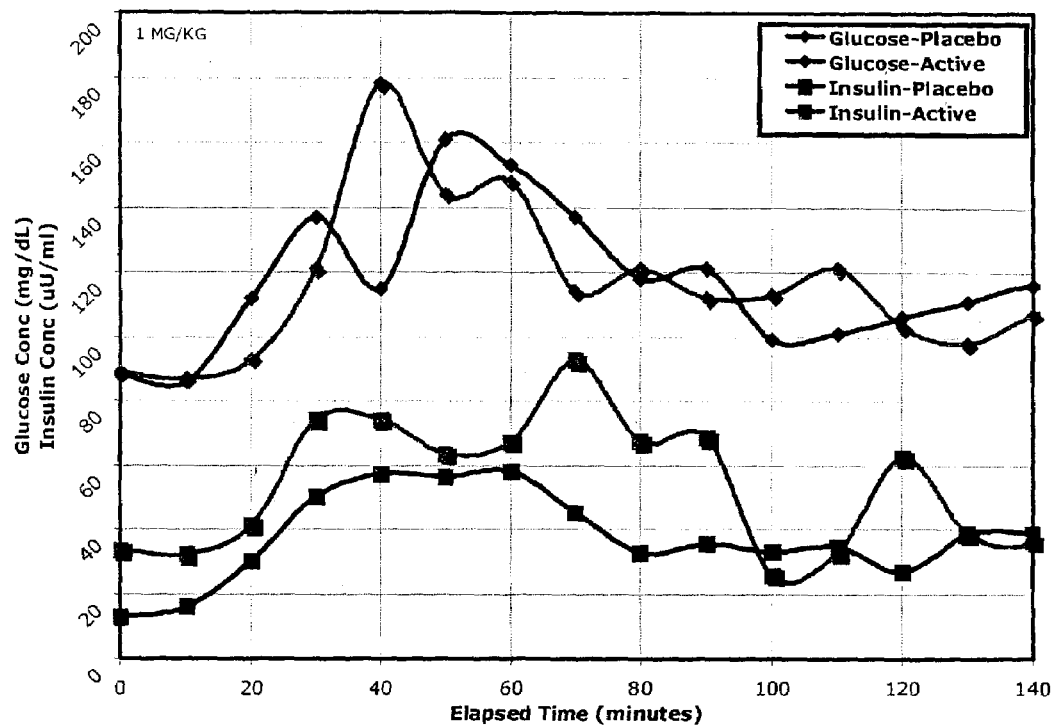
FIG. 10 represents a graph showing a schematic plot illustrating the effect of a composition of bio-active compounds derived from fenugreek seed non-debitterized extract containing one (1) mg 4-hydroxyisoleucine per kg body weight on the glucose concentration and insulin concentration in a first human subject conducted pursuant to one presently preferred embodiment or a method of the present invention.

Referring specifically to FIG. 10, a schematic plot illustrates the placebo portion and active portion results in the first human subject. The active portion contained 75 g of glucose in 300 mL of water as well as one presently preferred embodiment of the present invention comprising a unique, high-potency fenugreek seed non-debitterized extract of bio-active compounds (e.g., Promilin™) at a concentration of 1 mg 4-hydroxyisoleucine per kg body weight.

As depicted in the graphical illustration, measurements taken of the insulin activity and glucose level in the first human subject over the course of the experiment indicate that the composition of bio-active compounds derived from fenugreek seed (e.g., Promilin™) affects the level of insulin and glucose in the human subject. It is readily seen that after time equals zero the insulin activity levels of the first human subject were higher for the active solution containing the bio-active compounds and that the glucose levels are lower.

Figure 11:
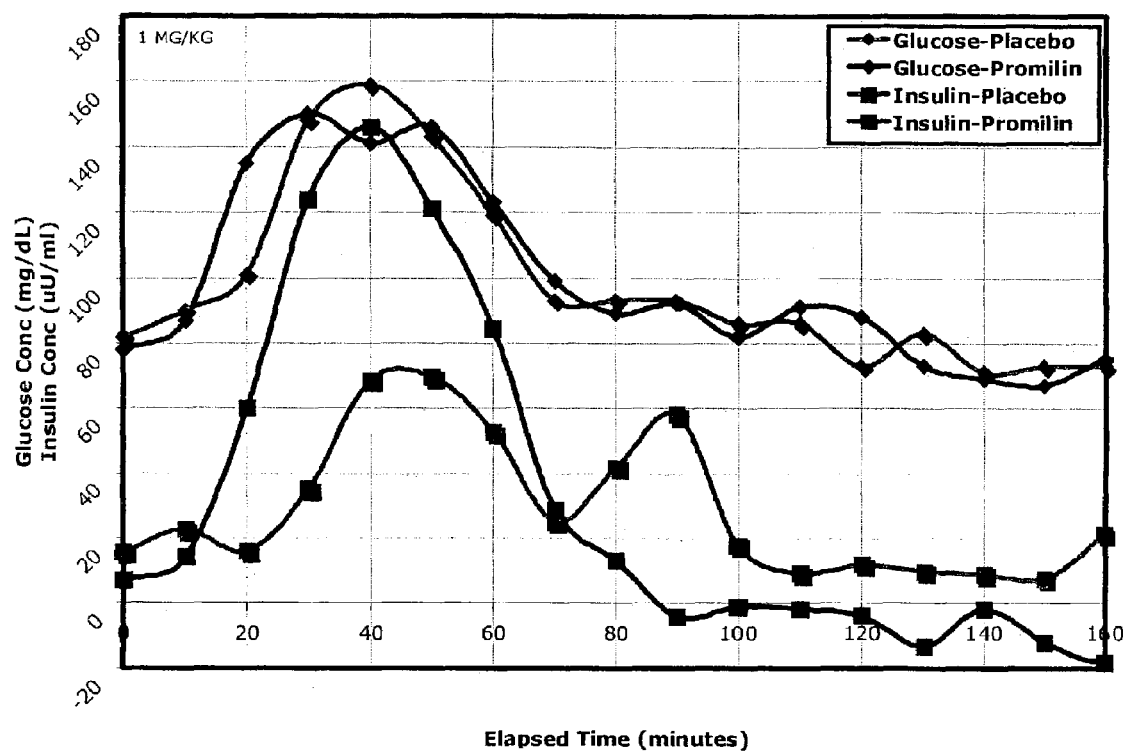
FIG. 11 represents a graph showing a schematic plot illustrating the effect of a composition of bio-active compounds derived from fenugreek seed non-debitterized extract containing one (1) mg 4-hydroxyisoleucine per kg body weight on the glucose concentration and insulin concentration in a second human subject conducted pursuant to one presently preferred embodiment of a method of the present invention.

Referring now to FIG. 11, a schematic plot illustrates the placebo portion and active portion results in a second human subject. The active portion contained 75 g of glucose in 300 mL of water as well as one presently preferred embodiment of the present invention comprising a unique, high-potency fenugreek seed non-debitterized extract of a composition of bio-active compounds derived from fenugreek seed (e.g., Promilin™) at a concentration of 1 mg 4-hydroxyisoleucine per kg body weight.

As depicted in the graphical illustration, measurements taken of the insulin activity and glucose level in the second human subject over the course of the experiment indicate that the composition of bio-active compounds (e.g., Promilin™) affects the level of insulin and glucose in the human subject. It is readily seen that after time equals zero the insulin activity levels of the second human subject rose remarkably beyond pre-administration levels for measurements taken following administration of the active solution containing the bio-active components and that the glucose levels are lower.

It is readily appreciated that the tests conducted on the first and second human subjects to evaluate the results of exposure to a composition of bio-active compounds derived from fenugreek seed extract prepared in accordance with the fenugreek seed preparation process (e.g., Promilin™) may be configured or modified to apply to any number of embodiments for practicing the present invention which are consistent with the spirit and scope of the present invention. It is intended, therefore, that the examples provided herein be viewed as exemplary of the principles of the present invention, and not as restrictive to a particular structure or method for implementing those principles.

EXAMPLE IV

Debitterized Fenugreek Seed Extract in Humans—4 mg 4-hydroxyisoleucine/kg

Figure 12:
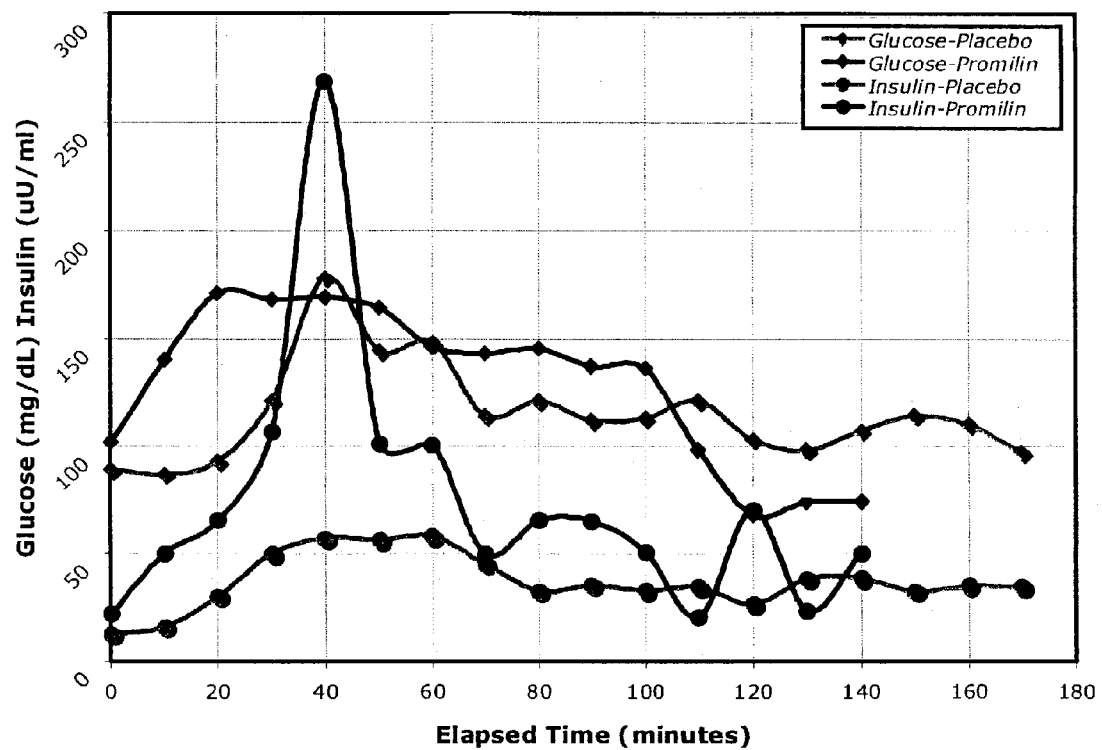
FIG. 12 represents a graph showing a schematic plot illustrating the effect of a composition of bio-active compounds derived from fenugreek seed debitterized extract containing four (4) mg 4-hydroxyisoleucine per kg body weight on the glucose concentration and insulin concentration in the first human subject conducted pursuant to one presently preferred embodiment of a method of the present invention.

As seen in FIG. 12, a schematic plot illustrates the placebo portion and active portion results in a first human subject. The active portion contained 75 g of glucose in 300 mL of water as well as one presently preferred embodiment of the present invention comprising a unique, high-potency fenugreek seed debitterized extract of bio-active compounds (e.g., Promilin™) at a concentration of 4 mg 4-hydroxyisoleucine per kg body weight.

As depicted in the graphical illustration, measurements taken of the insulin activity and glucose level in the first human subject over the course of the experiment indicate that the composition of bio-active compounds derived from fenugreek seed (e.g., Promilin™) affect the level of insulin and glucose in the first human subject. It is readily seen that after time equals zero the insulin activity levels of the first human subject rose remarkably beyond pre-administration levels for measurements taken following administration of the active solution containing the bio-active components and that the glucose levels are lower.

Figure 13:
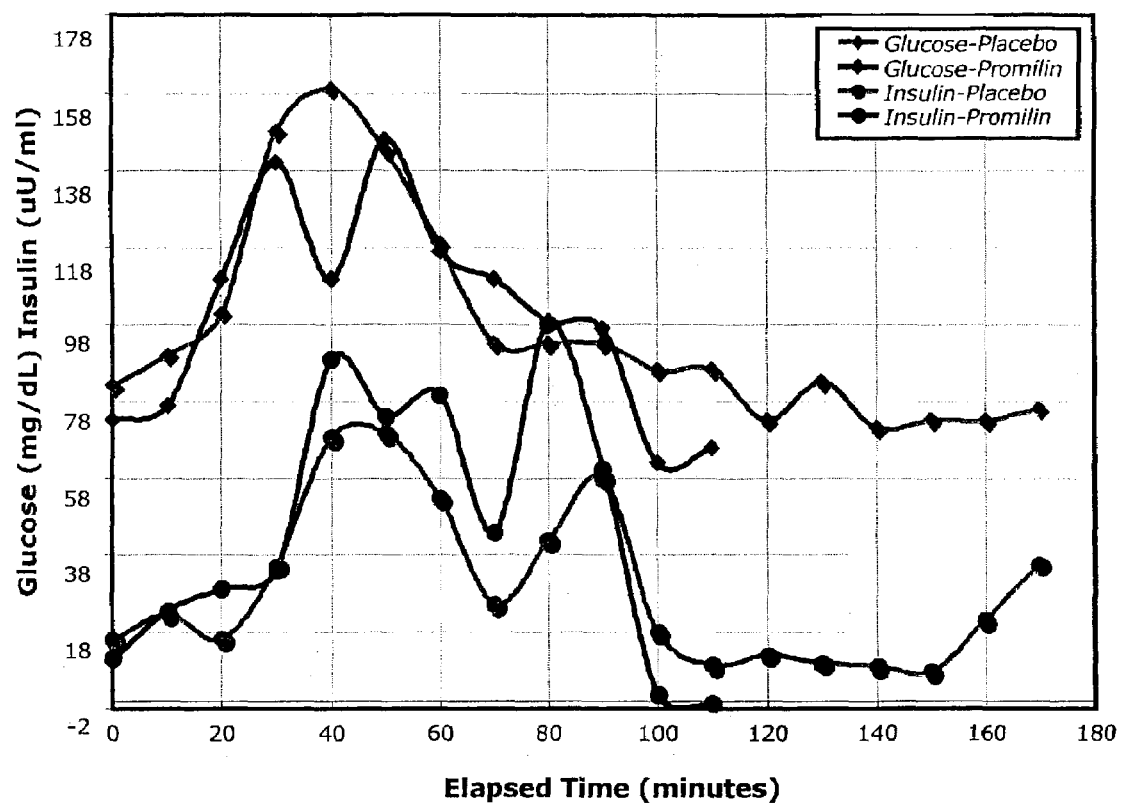
FIG. 13 represents a graph showing a schematic plot illustrating the effect of a composition of bio-active compounds derived from fenugreek seed debitterized extract containing four (4) mg 4-hydroxyisoleucine per kg body weight on the glucose concentration and insulin concentration in the second human subject conducted pursuant to one presently preferred embodiment of a method of the present invention.

Referring now to FIG. 13, a schematic plot illustrates the placebo portion and active portion results in a second human subject. The active portion contained 75 g of glucose in 300 mL of water as well as one presently preferred embodiment of the present invention comprising a unique, high-potency fenugreek seed debitterized extract of bio-active compounds (e.g., Promilin™) at a concentration of 4 mg 4-hydroxyisoleucine per kg body weight.

As depicted in the graphical illustration, measurements taken of the insulin activity and glucose level in the second human subject over the course of the experiment indicate that the composition of bio-active compounds derived from fenugreek seed (e.g., Promilin™) affect the level of insulin and glucose in the second human subject. It is readily seen that after time equals zero the insulin activity levels of the second human subject rose remarkably beyond pre-administration levels for measurements taken following administration of the active solution containing the bio-active compounds and that the glucose levels are lower.

Figure 14:
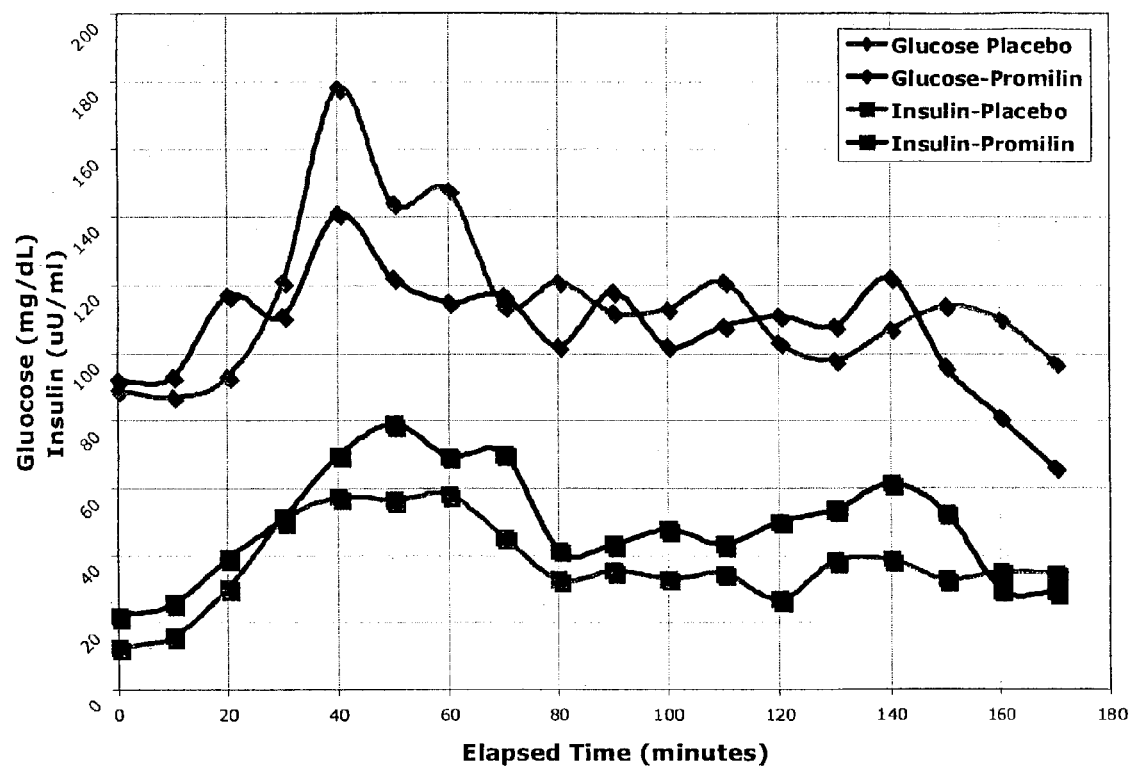
FIG. 14 represents a graph showing another schematic plot illustrating the effect of a composition of bio-active compounds derived from fenugreek seed debitterized extract containing four (4) mg 4-hydroxyisoleucine per kg body weight on the glucose concentration and insulin concentration in the first human subject conducted pursuant to one presently preferred embodiment of a method of the present invention.

An alternative presently preferred embodiment of the present invention using a debitterized extract at 4 mg 4-hydroxyisoleucine per mL is graphically represented in FIG. 14. As shown, a schematic plot illustrates the placebo portion and active portion results in a first human subject. The active portion contained 75 g of glucose in 300 mL of water as well as an alternative embodiment of the present invention comprising a unique, high-potency fenugreek seed debitterized extract of bio-active compounds (e.g., Promilin™) at a concentration of four (4) mg 4-hydroxyisoleucine per kg body weight.

As depicted in the graphical illustration, measurements taken of the insulin activity and glucose level in the first human subject over the course of the experiment indicate that the composition of bio-active compounds derived from fenugreek seed (e.g., Promilin™) affect the level of insulin and glucose in the first human subject. It is readily seen that after time equals zero the insulin activity levels of the first human subject were higher for the active solution containing the bio-active compounds and that the glucose levels are lower.

Figure 15:
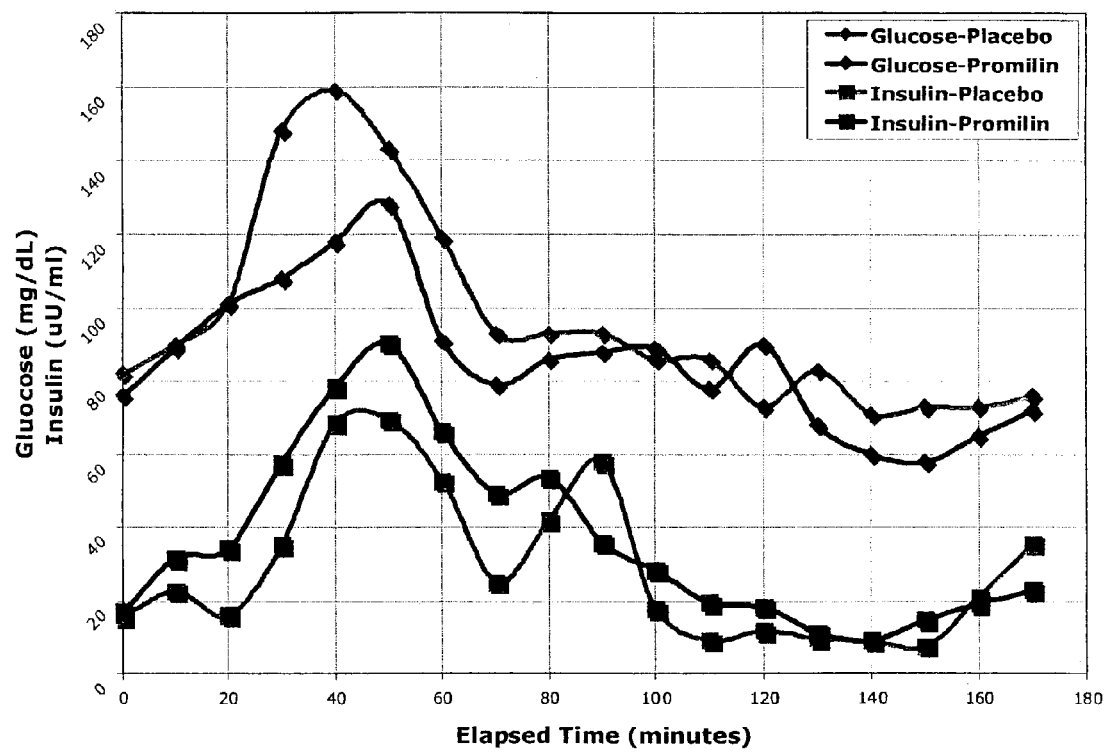
FIG. 15 represents a graph showing another schematic plot illustrating the effect of a composition of bio-active compounds derived from fenugreek seed debitterized extract containing four (4) mg 4-hydroxyisoleucine per kg body weight on the glucose concentration and insulin concentration in the second human subject conducted pursuant to one presently preferred embodiment of a method of the present invention.

Referring now to FIG. 15, a schematic plot illustrates the placebo portion and active portion results in a second human subject using a debitterized extract at 4 mg 4-hydroxyisoleucine per mL. The active portion contained 75 g of glucose in 300 mL of water as well as an alternative embodiment of the present invention comprising a unique, high-potency fenugreek seed debitterized extract of bio-active compounds (e.g., Promilin™) at a concentration of four (4) mg 4-hydroxyisoleucine per kg body weight.

As depicted in the illustration, measurements taken of the insulin activity and glucose level in the second human subject over the course of the experiment indicate that the composition of bio-active compounds derived from fenugreek seed (e.g., Promilin™) affect the level of insulin and glucose in the second human subject. It is readily seen that after time equals zero the insulin activity levels of the second human subject rose remarkably beyond pre-administration levels for measurements taken following administration of the active solution containing the bio-active compounds and that the glucose levels are lower.

It is readily appreciated that the tests conducted on the first and second human subjects to evaluate the results of exposure to a composition of bio-active compounds derived from fenugreek seed extract prepared in accordance with the fenugreek seed preparation process of a preferred or alternate presently preferred embodiment of the present invention (e.g., Promilin™) may be configured or modified to apply to any number of embodiments for practicing the present invention which are consistent with the spirit and scope of the present invention. It is intended, therefore, that the examples provided herein be viewed as exemplary of the principles of the present invention, and not as restrictive to a particular structure or method for implementing those principles.

EXAMPLE V

Non-debitterized fenugreek seed extract in humans—4 mg 4-hydroxyisoleucine/kg

Figure 16:
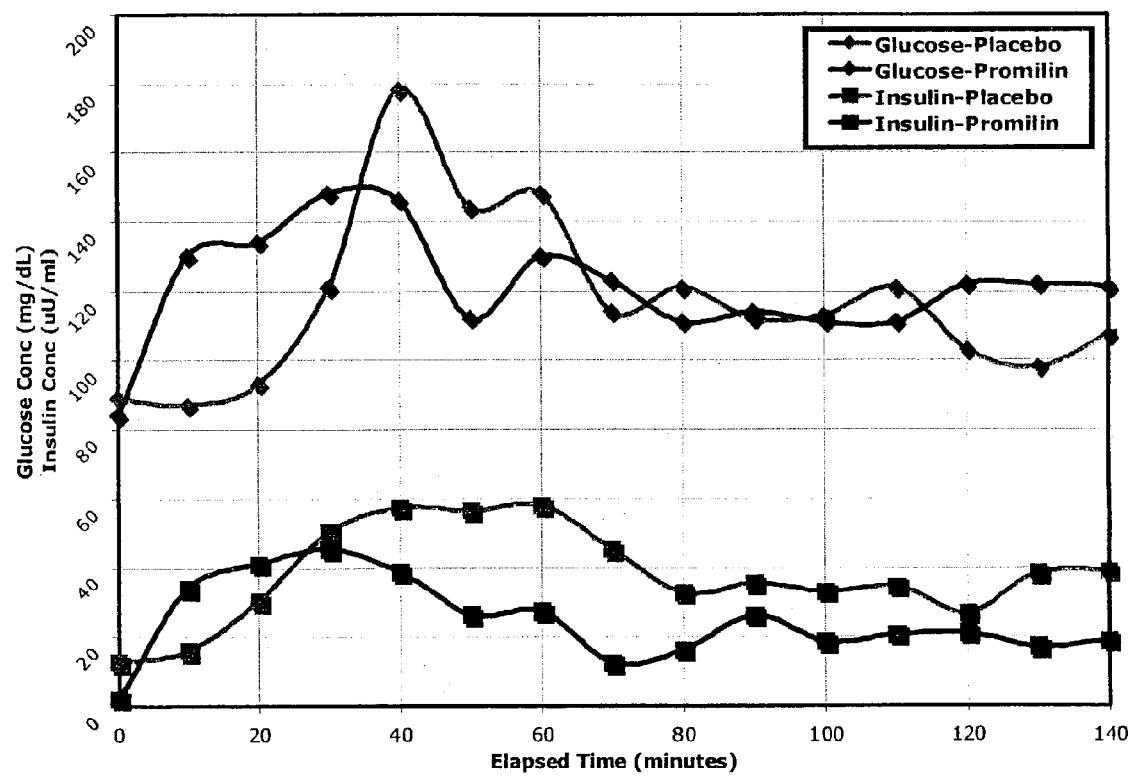
FIG. 16 represents a graph showing yet another schematic plot illustrating the effect of a composition of bio-active compounds derived from fenugreek seed non-debitterized extract containing four (4) mg 4-hydroxyisoleucine per kg body weight on the glucose concentration and insulin concentration in the first human subject conducted pursuant to one presently preferred embodiment of a method of the present invention.

Referring now to FIG. 16, a schematic plot illustrates the placebo portion and active portion results in a first human subject. The active portion contained 75 g of glucose in 300 mL of water as well as one presently preferred embodiment of the present invention comprising a unique, high-potency fenugreek seed non-debitterized extract of bio-active compounds (e.g., Promilin™) at a concentration of 4 mg 4-hydroxyisoleucine per kg body weight.

As depicted in the graphical illustration, measurements taken of the insulin activity and glucose level in the first human subject over the course of the experiment indicate that the composition of bio-active compounds derived from fenugreek seed (e.g., Promilin™) affect the level of insulin and glucose in the first human subject. It is readily seen that after time equals zero the insulin activity levels of the first human subject were higher for the active solution containing the bio-active components and that the glucose levels are lower.

Figure 17:
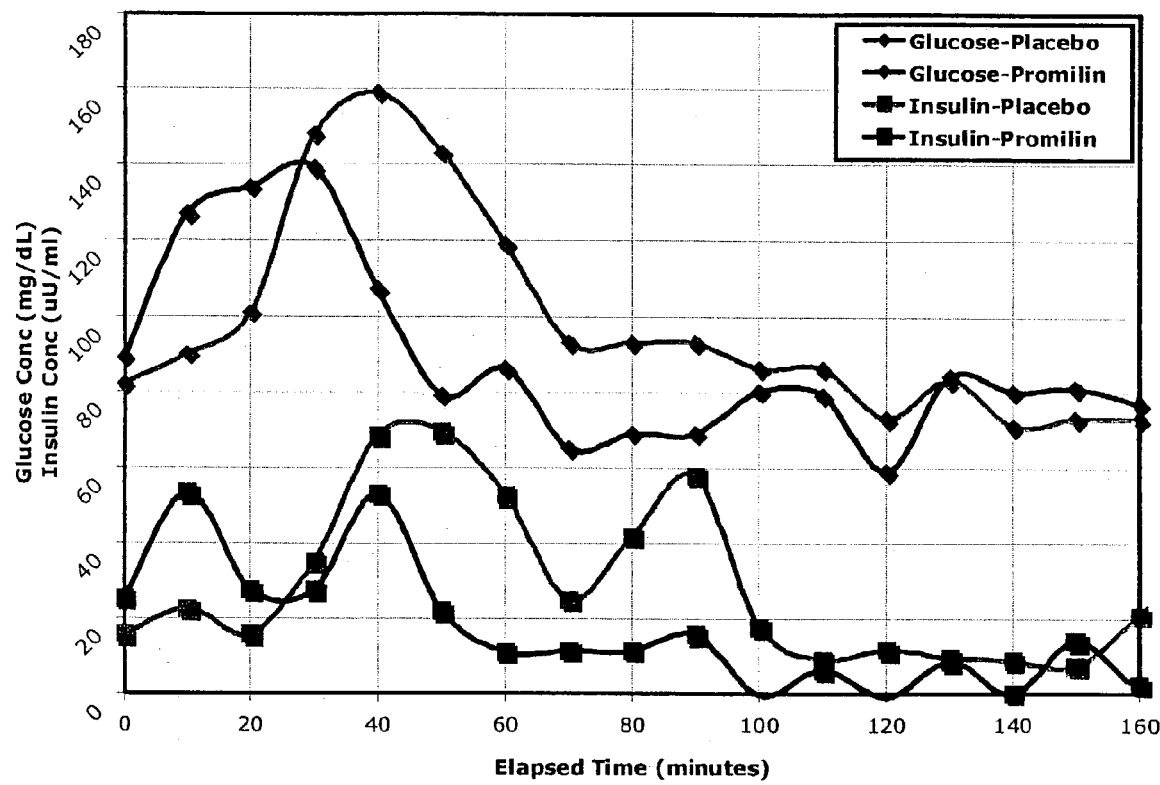
FIG. 17 represents a graph showing yet another schematic plot illustrating the effect of a composition of bio-active compounds derived from fenugreek seed non-debitterized extract containing four (4) mg 4-hydroxyisoleucine per kg body weight on the glucose concentration and insulin concentration in the second human subject conducted pursuant to one presently preferred embodiment of a method of the present invention.

A schematic plot, as shown in FIG. 17, illustrates the placebo portion and active portion results in a second human subject. The active portion contained 75 g of glucose in 300 mL of water as well as one presently preferred embodiment of the present invention comprising a unique, high-potency fenugreek seed non-debitterized extract of bio-active compounds (e.g., Promilin™) at a concentration of 4 mg 4-hydroxyisoleucine per kg body weight.

As depicted in the graphical illustration, measurements taken of the insulin activity and glucose level in the second human subject over the course of the experiment indicate that the composition of bio-active compounds derived from fenugreek seed (e.g., Promilin™) affect the level of insulin and glucose in the second human subject. It is readily seen that after time equals zero the insulin activity levels of the second human subject rose remarkably beyond pre-administration levels for measurements taken following administration of the active solution containing the bio-active components and that the glucose levels are lower.

It is readily appreciated that the tests conducted on the first and second human subjects to evaluate the results of exposure to a composition of bio-active compounds derived from fenugreek seed extract prepared in accordance with the fenugreek seed preparation process of a preferred or alternate presently preferred embodiment of the present invention (e.g., Promilin™) may be configured or modified to apply to any number of embodiments for practicing the present invention which are consistent with the spirit and scope of the present invention. It is intended, therefore, that the examples provided herein be viewed as exemplary of the principles of the present invention, and not as restrictive to a particular structure or method for implementing those principles.

EXAMPLE VI

Debitterized Fenugreek Seed Extract in Humans—9 mg 4-hydroxyisoleucine/kg

Figure 18:
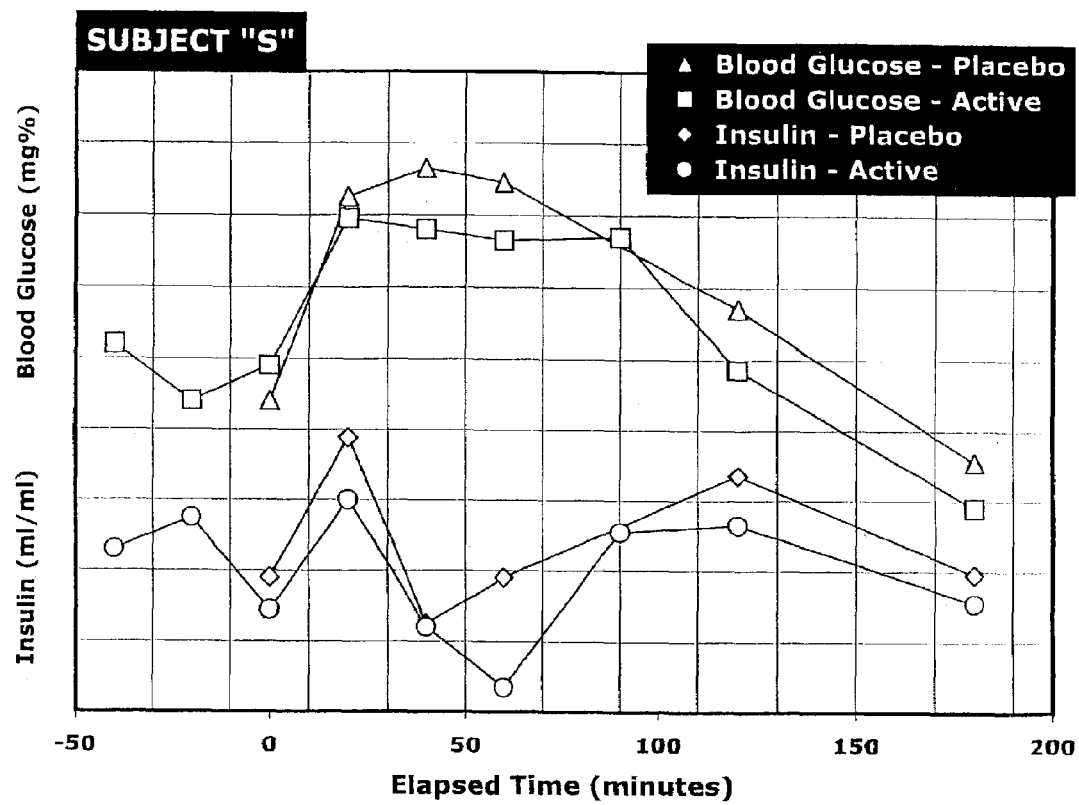
FIG. 18 represents a graph showing a schematic plot illustrating the effect of a composition of bio-active compounds derived from fenugreek seed non-debitterized extract containing nine (9) mg 4-hydroxyisoleucine per kg body weight on the glucose concentration and insulin concentration in a first human subject conducted pursuant to one presently preferred embodiment of a method of the present invention.

Referring now to FIG. 18, a schematic plot illustrates the placebo portion and active portion results in a first human subject. The active portion contained 75 g of glucose in 300 mL of water as well as one presently preferred embodiment of the present invention comprising a unique, high-potency fenugreek seed debitterized extract of bio-active compounds (e.g., Promilin™) at a concentration of 9 mg 4-hydroxyisoleucine per kg body weight.

As depicted in the graphical illustration, measurements taken of the insulin activity and glucose level in the first human subject over the course of the experiment indicate that the composition of bio-active compounds derived from fenugreek seed (e.g., Promilin™) affect the level of insulin and glucose in the first human subject. It is readily seen that after time equals zero the insulin activity levels of the first human subject were higher for the active solution containing the bio-active components and that the glucose levels are lower.

Figure 19:
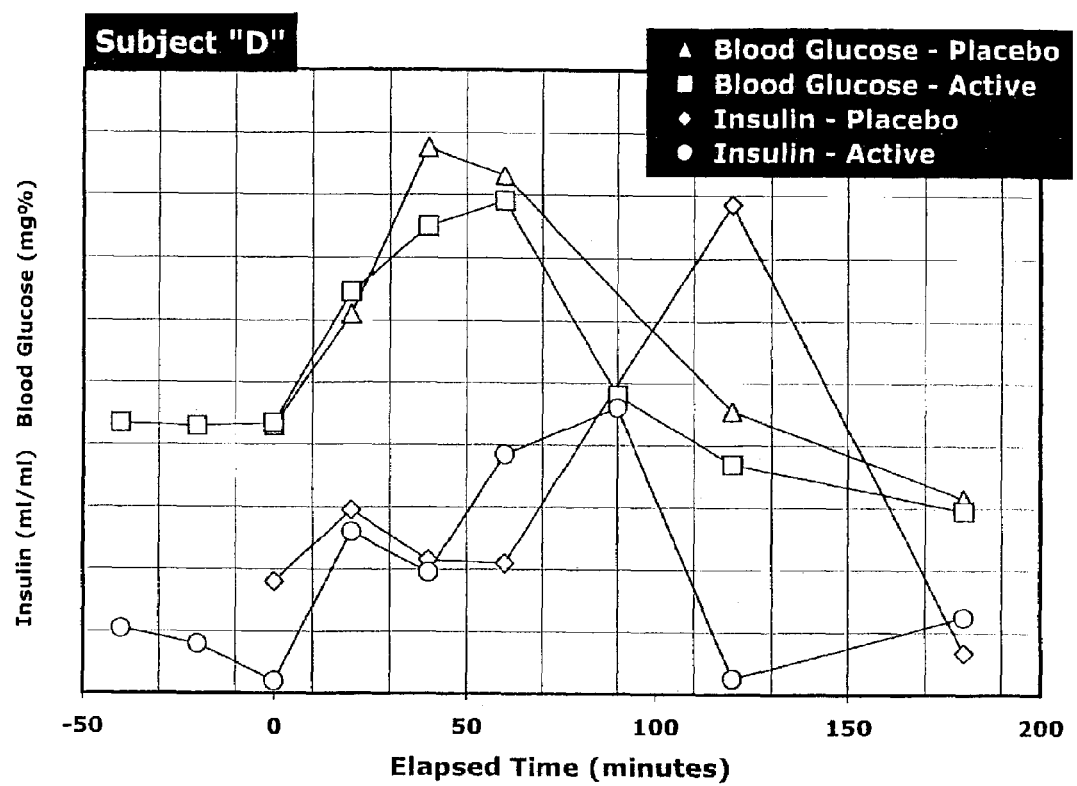
FIG. 19 represents a graph showing a schematic plot illustrating the effect of a composition of bio-active compounds derived from fenugreek seed non-debitterized extract containing nine (9) mg 4-hydroxyisoleucine per kg body weight on the glucose concentration and insulin concentration in a third human subject conducted pursuant to one presently preferred embodiment of a method of the present invention.

Referring now to FIG. 19, a schematic plot illustrates the placebo portion and active portion results in a third human subject. The active portion contained 75 g of glucose in 300 mL of water as well as one presently preferred embodiment of the present invention comprising a unique, high-potency fenugreek seed debitterized extract of bio-active compounds (e.g., Promilin™) at a concentration of 9 mg 4-hydroxyisoleucine per kg body weight.

As depicted in the graphical illustration, measurements taken of the insulin activity and glucose level in the third human subject over the course of the experiment indicate that the composition of bio-active compounds derived from fenugreek seed (e.g., Promilin™) affect the level of insulin and glucose in the third human subject. It is readily seen that after time equals zero the insulin activity levels of the third human subject rose remarkably beyond pre-administration levels for measurements taken following administration of the active solution containing the bio-active components and that the glucose levels are lower.

It is readily appreciated that the tests conducted on the first and third human subjects to evaluate the results of exposure to a composition of bio-active compounds derived from fenugreek seed extract prepared in accordance with the fenugreek seed preparation process of a preferred or alternate presently preferred embodiment of the present invention (e.g., Promilin™) may be configured or modified to apply to any number of embodiments for practicing the present invention which are consistent with the spirit and scope of the present invention. It is intended, therefore, that the examples provided herein be viewed as exemplary of the principles of the present invention, and not as restrictive to a particular structure or method for implementing those principles.

It will be further appreciated that the novel compositions of bio-active compounds derived from fenugreek seeds of the present invention may be administered orally, parenterally, sublingual, topical, transdermal, intramuscular, or inhalation, and may also contain excipients chosen in accordance with the dosage form adopted. Moreover, the dosage of the extract compositions given to an individual may vary on the basis of several considerations without departing from the spirit and scope of the present invention and will, accordingly, depend on the targeted individual's particular case to be treated.

From the above discussion, it will be appreciated that the present invention provides novel compositions and methods for the extraction and separation of bio-active compounds derived from fenugreek seeds which are capable of facilitating increase glucose induced insulin levels, enhancing insulin sensitivity, stimulating the function of glucose transport factor 4. In preferred design, the novel methods for extracting and separating the bio-active compounds derived from fenugreek seeds produces a high potency and quality extract yield that is economical and efficient to produce.

Unlike the prior art, the present invention provides novel compositions and methods for extracting and separating bio-active compounds derived from fenugreek seeds including, without limitation, 4-hydroxyisoleucine, arginine, aspartate, threonine, serine, glutamate, proline, glycine, alanine, cysteine, valine, methionine, isoleucine, leucine, tryptophan, phenylalanine, ornithine, lysine, histidine and gamma-aminobutyrate. These novel extracted compositions from fenugreek seeds are capable of independently stimulating glucose transport proteins and facilitating the transport of glucose into muscles or, in the alternative, work synergistically with insulin to stimulate glucose transport proteins and facilitate the transport of glucose into muscles.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A composition of bio-active compounds for supporting metabolism and transportation of glucose and carbohydrates into muscle cells, said composition comprising an amino acid content including 4-hydroxyisoleucine and cysteine, wherein said 4-hydroxyisoleucine comprises an amount between about 60% and about 70% of a total weight of said amino acid content and said cysteine comprises between about 1% and about 2% of the total weight of the amino acid content of the composition.

2. The composition as defined in claim 1, wherein said 4-hydroxyisoleucine and said cysteine are extracted from fenugreek seeds (*Trigonella foenum graecum*).

3. The composition as defined in claim 1, further comprising arginine in an amount between about 2.4% and about 2.7% of said total weight of said amino acid content of said composition.

4. The composition as defined in claim 1, further comprising aspartate in an amount between about 4% and about 5% of said total weight of said amino acid content of said composition.

5. The composition as defined in claim 1, further comprising threonine in an amount between about 0.90% and about 1% of said total weight of said amino acid content of said composition.

6. The composition as defined in claim 1, further comprising serine in an amount between about 4% and about 12% of said total weight of said amino acid content of said composition.

7. The composition as defined in claim 1, further comprising glutamate in amount between about 6% and about 8% of said total weight of said amino acid content of said composition.

8. The composition as defined in claim 1, further comprising glycine in an amount between about 2% and about 3% of said total weight of said amino acid content of said composition.

9. The composition as defined in claim 1, further comprising alanine in an amount between about 3% and about 4% of said total weight of said amino acid content of said composition.

10. The composition as defined in claim 1, further comprising valine in an amount between about 1% and about 1.5% of said total weight of said amino acid content of said composition.

11. The composition as defined in claim 1, further comprising methionine in an amount between about 0.35% and about 0.60% of said total weight of said amino acid content of said composition.

12. The composition as defined in claim 1, further comprising isoleucine in an amount greater than 0.5% of said total weight of said amino acid content of said composition.

13. The composition as defined in claim 1, further comprising histidine in an amount between about 0.35% and about 0.40% of said total weight of said amino acid content of said composition.

14. The composition as defined in claim 1, wherein said composition comprises an effective amount of said amino acid content sufficient to stimulate a glucose transport factor.

15. The composition as defined in claim 14, wherein said glucose transport factor comprises glucose transport factor 4.

16. The composition as defined in claim 1, wherein said composition functions independently of insulin.

17. A composition of bio-active compounds for supporting metabolism and transportation of glucose and carbohydrates into muscle cells, said composition comprising an amino acid content including 4-hydroxyisoleucine end glutamate, wherein said 4-hydroxyisoleucine comprises an amount between about 60% and about 70% of a total weight of said amino acid content and said glutamate comprises an amount between about 6% and about 8% of the total weight of said the amino acid complex of the composition.

18. The composition as defined in claim 1, wherein said 4-hydroxyisoleucine and said glutamate are extracted from fenugreek seeds (Trigonella foenum graecum).

19. The composition as defined in claim 17, further comprising aspartate in an amount between about 4% and about 5% of said total weight of said amino acid content of said composition.

20. The composition as defined in claim 17, further comprising serine in an amount between about 4% and about 12% of said total weight of said amino acid content of said composition.

21. The composition as defined in claim 17, further comprising alanine in an amount between about 3% and about 4% of said total weight of said amino acid content of said composition.

22. The composition as defined in claim 17, further comprising arginine in an amount between about 2.4% and about 2.7% of said total weight of said amino acid content of said composition.

23. The composition as defined in 17, further comprising cysteine in an amount between about 1% and about 2% of said total weight of said amino acid content of said composition.

24. The composition as defined in claim 17, further comprising glycine in an amount between about 2% and about 3% of said total weight of said amino acid content of said composition.

25. The composition as defined in claim 17, further comprising isoleucine in an amount greater than 0.5% of said total weight of said amino acid content of said composition.

26. The composition as defined in claim 17, further comprising threonine in an amount between about 0.90% and about 1% of said total weight of said amino acid content of said composition.

27. The composition as defined in claim 17, further comprising methionine in an amount between about 0.35% and about 0.60% of said total weight of said amino add content of said composition.

28. The composition as defined in claim 17, further comprising histidine in an amount between about 0.35% and about 0.40% of said total weight of said amino acid content of said composition.

29. The composition as defined in claim 17, further comprising valine in an amount between about 1% and about 1.5% of said total weight of said amino acid content of said composition.

30. The composition as defined in claim 17, wherein said composition comprises an effective amount of said amino acid content sufficient to stimulate a glucose transport factor.

31. The composition as defined in claim 30, wherein said glucose transport factor comprises glucose transport factor 4.

32. The composition as defined in claim 17, wherein said composition functions independently of insulin.

33. A composition of bio-active compounds for supporting transportation of glucose and carbohydrates into muscle cells, said composition comprising an amino acid content including 4-hydroxyisoleucine, glutamate, and aspartate, wherein said 4-hydroxyisoleucine comprises an amount between about 60% and about 70% of a total weight of said amino avid content, the glutamate comprises an amount between about 6% and about 8% of the total weight of the amino acid content, and the aspartate comprises an amount between about 4% and about 5% of the total weight of the amino acid content of the composition.

34. The composition as defined in claim 33, wherein said 4-hydroxyisoleucine, said glutamate, and said aspartate are extracted from fenugreek seeds (Trigonella foenum graecum).

35. The composition as defined in claim 33, further comprising cysteine in an amount between about 1% and about 2% of the total weight of said amino acid content of said composition.

36. The composition as defined in claim 33, further comprising serine in an amount between about 4% and about 12% of said total weight of said amino acid content of said composition.

37. The composition as defined in claim 33, further comprising alanine in an amount between about 3% and about 4% of said total weight of said amino acid content of said composition.

38. The composition as defined in claim 33, further comprising arginine in an amount between about 2.4% and about 2.7% of said total weight of said amino acid content of said composition.

39. The composition as defined in claim 33, further comprising glycine in an amount between about 2% and about 3% of the total weight of said amino acid content of said composition.

40. The composition as defined in claim 33, further comprising isoleucine in an amount greater than 0.5% of the total weight of said amino acid content of said composition.

41. The composition as defined in claim 33, further comprising threonine in an amount between about 0.90% and about 1% of the total weight of said amino acid content of said composition.

42. The composition as defined in claim 33, further comprising methionine in an amount between about 0.35% and about 0.60% of the total weight of said amino acid content of said composition.

43. The composition as defined in claim 33, further comprising histidine in an amount between about 0.35% and about 0.40% of the total weight of said amino acid content of said composition.

44. The composition as defined in claim 33, further comprising valine in an amount between about 1% and about 1.5% of the total weight of said amino acid content of said composition.

45. The composition as defined in claim 33, wherein said composition comprises an effective amount of said amino acid content sufficient to stimulate a glucose transport factor.

46. The composition as defined in claim 45, wherein said glucose transport factor comprises glucose transport factor 4.

47. The composition as defined in claim 33, wherein said composition functions independently of insulin.

48. A composition of bio-active compounds for supporting metabolism and transportation of glucose and carbohydrates into muscle cells, said composition comprising an amino acid content including 4-hydroxyisoleucine, cysteine, and glutamate, wherein said 4-hydroxyisoleucine comprises an amount between about 60% and about 70% of a total weight of said amino acid content, said cysteine comprises an amount between about 1% and about 2% of a total weight of said amino acid content, and said glutamate comprises an amount between about 6% and about 3% of said total weight of the amino acid content of the composition.

49. The composition as defined in claim 48, further comprising arginine in an amount between about 2.4% and about 2.7% of said total weight of said amino acid content of said composition.

50. The composition as defined in claim 48, further comprising aspartate in an amount between about 4% and about 5% of said total weight of said amino acid content of said composition.

51. The composition as defined in claim 48, further comprising threonine in an amount between about 0.90% and about 1% of said total weight of said amino acid content of said composition.

52. The composition as defined in claim 48, further comprising serine in an amount between about 4% and about 12% of said total weight of said amino acid content of said composition.

53. The composition as defined in claim 48, further comprising alanine in an amount between about 3% and about 4% of said total weight of said amino acid content of said composition.

54. The composition as defined in claim 48, further comprising valine in an amount between about 1% and about 1.5% of said total weight of said amino acid content of said composition.

55. The composition as defined in claim 48, further comprising methionine in an amount between about 0.35% and about 0.60% of said total weight said amino acid content of said composition.

56. The composition as defined in claim 48, further comprising isoleucine in an amount greater than 0.5% of said total weight of said amino acid content of said composition.

57. The composition as defined in claim 48, further comprising histidine in an amount between about 0.35% and about 0.40% of said total weight of said amino acid content of said composition.

* * * * *

UNITED STATES PATENT AND TRADEMARK OFFICE
CERTIFICATE OF CORRECTION

PATENT NO. : 7,338,675 B2  Page 1 of 1
APPLICATION NO. : 10/434444
DATED : March 4, 2008
INVENTOR(S) : Steve S. Lee et al.

It is certified that error appears in the above-identified patent and that said Letters Patent is hereby corrected as shown below:

- column 3, line 60, please delete "seine", and insert therefor -- serine --.
- column 4, line 34, please delete "seine", and insert therefor -- serine --.
- column 25, line 55, please delete "end", and insert therefor -- and --.
- column 25, line 60, please delete "said".
- column 25, line 61, please delete "1", and insert therefor -- 17 --.
- column 26, line 31, please delete "add", and insert therefor -- acid --.
- column 26, line 55, please delete "avid", and insert therefor -- acid --.
- column 28, line 7, please delete "3%", and insert therefor -- 8% --.

Signed and Sealed this

Second Day of September, 2008

JON W. DUDAS
*Director of the United States Patent and Trademark Office*